United States Patent
Kinugasa

(10) Patent No.: US 9,291,542 B2
(45) Date of Patent: Mar. 22, 2016

(54) PARTICLE DETECTING DEVICE AND PARTICLE DETECTING METHOD

(71) Applicant: Azbil Corporation, Tokyo (JP)

(72) Inventor: Seiichiro Kinugasa, Tokyo (JP)

(73) Assignee: AZBIL CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/573,458

(22) Filed: Dec. 17, 2014

(65) Prior Publication Data

US 2015/0177144 A1 Jun. 25, 2015

(30) Foreign Application Priority Data

Dec. 20, 2013 (JP) ................................ 2013-264600

(51) Int. Cl.

| G01N 21/64 | (2006.01) |
|---|---|
| G01N 15/06 | (2006.01) |
| G01N 15/04 | (2006.01) |
| G01N 15/14 | (2006.01) |
| G01N 15/00 | (2006.01) |
| G01N 21/53 | (2006.01) |

(52) U.S. Cl.
CPC ........ *G01N 15/1434* (2013.01); *G01N 15/1459* (2013.01); *G01N 21/53* (2013.01); *G01N 21/645* (2013.01); *G01N 2015/0046* (2013.01); *G01N 2021/6421* (2013.01)

(58) Field of Classification Search
CPC ........ G01N 21/64; G01N 15/06; G01N 15/04
See application file for complete search history.

(56) References Cited

U.S. PATENT DOCUMENTS

| 7,295,319 B2 | 11/2007 | Kajii |
| 2004/0262501 A1 | 12/2004 | Kajii |

(Continued)

FOREIGN PATENT DOCUMENTS

| JP | 2003-139707 | 5/2003 |
| JP | 2008-530583 | 8/2008 |

(Continued)

OTHER PUBLICATIONS

Norio Hasegawa, et al., "Instantaneous Bioaerosol Detection Technology and Its Application", azbil Technical Review, Yamatake Corporation, pp. 2-7 Dec. 2009.

(Continued)

*Primary Examiner* — David Porta
*Assistant Examiner* — Faye Boosalis
(74) *Attorney, Agent, or Firm* — Troutman Sanders LLP

(57) ABSTRACT

A particle detecting device includes: a light source that illuminates, with an excitation beam, a fluid that contains a plurality of particles; a fluorescence measuring instrument that measures, at at least two different wavelengths, fluorescence that is produced in a region that is illuminated by the excitation beam; a scattered light measuring instrument that measures scattered light that is produced in a region that is illuminated by the excitation beam; an interference status evaluating portion that evaluates whether the scattered light that is measured is producing constructive interference or producing destructive interference; and a particle counting portion that counts a plurality of particles depending on the measured interference of the measured light, and counts fluorescent particles that are subject to detection, from among the plurality of particles, based on a wavelength of fluorescent measured.

10 Claims, 33 Drawing Sheets

(56) References Cited

U.S. PATENT DOCUMENTS

2006/0238757 A1 10/2006 Silcott
2011/0019186 A1* 1/2011 Himmelhaus et al. ........ 356/317

FOREIGN PATENT DOCUMENTS

| | | |
|---|---|---|
| JP | 2011-083214 | 4/2011 |
| JP | 2012-086105 | 5/2012 |
| JP | 2013-117466 | 6/2013 |

OTHER PUBLICATIONS

S. A. Nizkorodov, et al., "Time-resolved fluorescence of NO2 in a Magnetic Field" Chemical Physics Letters 215 (6):662-667, Dec. 17, 1993.

Joel A. Thornton, et al., "Atmospheric NO2: In Situ Laser-Induced Fluorescence Detection at Parts per Trillion Mixing Ratios" Analytical Chemistry, 72(3):528-539, Feb. 1, 2000.

* cited by examiner

PARTICLE DETECTING DEVICE AND PARTICLE DETECTING METHOD

CROSS REFERENCE TO RELATED APPLICATION

This application claims priority under 35 U.S.C. §119 to Japanese Patent Application No. 2013-264600, filed on Dec. 20, 2013, the entire content of which being hereby incorporated herein by reference.

FIELD OF TECHNOLOGY

The present disclosure relates to an environment evaluating technology, and, in particular, relates to a particle detecting device and particle detecting method.

BACKGROUND

In clean rooms, such as bio clean rooms, airborne microorganism particles and non-microorganism particles are detected and recorded using particle detecting devices. See, for example, Japanese Unexamined Patent Application Publication No. 2011-83214, Published Japanese Translation of a PCT Application Originally filed in English 2008-530583, and N. Hasegawa, et al., *Instantaneous Bioaerosol Detection Technology and Its Application*, azbil Technical Review, 2-7, Yamatake Corporation, December 2009. The state of wear of the air-conditioning equipment of the clean room can be ascertained from the result of the particle detection. Moreover, a record of particle detection within the clean room may be added as reference documentation to the products manufactured within the clean room. Optical particle detecting devices draw in air from a clean room, for example, and illuminate the drawn-in air with light. If a particle is included in the gas, then the particle that is illuminated by the light will produce scattered light. Moreover, if the particle is a microorganism particle board a non-microorganism fluorescent particle, then the particle that is illuminated with light will emit fluorescence. The particle detecting device is thus able to detect particles in the air through measuring the scattered light and the fluorescent light. For example, if scattered light and florescent light are measured simultaneously, then the particle detecting device evaluates that there is a fluorescent particle. Moreover, if scattered light is measured but no florescent light is measured, the particle detecting device evaluates that there is a non-fluorescent particle. Moreover, there is the need for technologies for accurately detecting particles in a fluid outside of clean rooms as well. See, for example, Japanese Unexamined Patent Application Publication No. 2013-117466.

Given this, an aspect of the present disclosure is to provide a particle detecting device and particle detecting method wherein particles can be detected accurately.

SUMMARY

In an example of the present invention, a particle detecting device is summarized to include:
(a) a light source that illuminates, with an excitation beam, a fluid that contains a plurality of particles;
(b) a fluorescence measuring instrument that measures, at at least two different wavelengths, fluorescence that is produced in a region that is illuminated by the excitation beam;
(c) a scattered light measuring instrument that measures scattered light that is produced in a region that is illuminated by the excitation beam;
(d) an interference status evaluating portion that evaluates whether the scattered light that is measured is producing constructive interference or producing destructive interference; and
(e) a particle counting portion that counts a plurality of particles depending on the measured interference of the measured light, and counts fluorescent particles that are subject to detection, from among the plurality of particles, based on a wavelength of fluorescent measured. Note that a "fluid" includes "gases" and "liquids." "Fluorescent light" includes autofluorescent light.

The particle counting portion evaluates that a particle that emits fluorescent light is a fluorescent particle that is subject to detection if, for example, the wavelength of the fluorescent light that is measured is the same wavelength as the fluorescent light that is emitted by a fluorescent particle that is subject to detection, acquired in advance. Additionally, the particle counting portion evaluates that a particle that emits fluorescent light is not a fluorescent particle that is subject to detection if, for example, the wavelength of the fluorescent light that is measured is different from the same wavelength as the fluorescent light that is emitted by a fluorescent particle that is subject to detection, acquired in advance.

If, for example, the scattered light that is measured produces constructive interference and the lengths of the times over which the scattered light and the fluorescent light are measured are essentially equal, then the particle counting portion will evaluate that all of a plurality of particles is fluorescent particles. Moreover, if, for example, constructive interference is produced by the scattered light that is measured and the lengths of the times over which the scattered light and the fluorescent light are measured are different, then the particle counting portion will evaluate that some of the plurality of particles is fluorescent particles. Furthermore, if the scattered light that is measured produces constructive interference and no florescent light is measured, then the particle counting portion will evaluate that all of the plurality of particles is non-fluorescent particles.

If, for example, peaks of scattered light are measured multiple times due to destructive interference, the time at which florescent light began to be measured and the first time at which scattered light began to be measured are essentially equal, and the time at which the measurement of the fluorescent light ended and the last time at which the measurement of scattered light ended are essentially equal, then the particle counting portion evaluates that all of the plurality of particles is fluorescent particles. Moreover, if, for example, peaks of scattered light are measured multiple times due to destructive interference, the time at which florescent light began to be measured and the first time at which scattered light began to be measured are different, or the time at which the measurement of the fluorescent light ended and the last time at which the measurement of scattered light ended are different, then the particle counting portion evaluates that some of the plurality of particles is fluorescent particles. Furthermore, if peaks of scattered light are measured multiple times due to destructive interference and no florescent light is measured, then the particle counting portion evaluates that all of the plurality of particles is non-fluorescent particles.

If, for example, scattered light is measured over a prescribed time and temporal variation of the intensity of the scattered light is below that which is prescribed, then the interference status evaluating portion evaluates that the measured scattered light is not producing interference. Moreover, if scattered light is measured over a prescribed time and the temporal variation of the intensity of the scattered light is equal to or greater than that which is prescribed, then the interference status evaluating portion evaluates that the measured scattered light is producing constructive interference. Furthermore, if scattered light peaks are measured multiple times within a prescribed time interval, the interference status evaluating portion evaluates that the measured scattered light is producing destructive interference.

Moreover, in another example of the present invention, a particle detecting method is summarized to include:

(a) illuminating, with an excitation beam, a fluid that contains a plurality of particles;

(b) measuring, at least two different wavelengths, fluorescence that is produced in a region that is illuminated by the excitation beam;

(c) measuring scattered light that is produced in a region that is illuminated by the excitation beam;

(d) evaluating whether the scattered light that is measured is producing constructive interference or producing destructive interference; and (e) counting a plurality of particles depending on the measured interference of the measured light, and for counting fluorescent particles that are subject to detection, from among the plurality of particles, based on a wavelength of fluorescent measured.

The evaluation is that a particle that emits fluorescent light is a fluorescent particle that is subject to detection if, for example, the wavelength of the fluorescent light that is measured is the same wavelength as the fluorescent light that is emitted by a fluorescent particle that is subject to detection, acquired in advance. Additionally, the evaluation is that a particle that emits fluorescent light is not a fluorescent particle that is subject to detection if, for example, the wavelength of the fluorescent light that is measured is different from the same wavelength as the fluorescent light that is emitted by a fluorescent particle that is subject to detection, acquired in advance.

For example, if the measured scattered light is producing constructive interference and the lengths of times over which the scattered light and the fluorescent light are measured are essentially equal, then there is an evaluation that all of the plurality of particles is fluorescent particles. Moreover, if, for example, the measured light is producing constructive interference and the length of times over which the scattered light and the fluorescent light are measured are different, there is an evaluation that some of the plurality of particles is fluorescent particles. Moreover, if, for example, the measured scattered light is producing constructive interference and no florescent light is measured, then there is an evaluation that all of the plurality of particles is non-fluorescent particles.

If, for example, peaks for scattered light are measured multiple times due to destructive interference, the time of the beginning of measurement of the fluorescent light and the time of the beginning of measurement of the first scattered light are essentially equal, and the time of the end of measurement of fluorescent light and the time of the end of measurement of the last scattered light are essentially equal, then there is an evaluation that essentially all of the plurality of particles is fluorescent particles. Furthermore, if, for example, peaks for scattered light are measured multiple times due to destructive interference, and the time of the beginning of measurement of the fluorescent light and the time of the beginning of measurement of the first scattered light are different or the time of the end of measurement of the fluorescent light and the time of the end of measurement of the last scattered light are different, then there is an evaluation that some of the plurality of particles is fluorescent particles. Furthermore, if, for example, peaks for scattered light are measured multiple times due to destructive interference but no florescent light is measured, then there is an evaluation that all of the plurality of particles is non-fluorescent particles.

If, for example, scattered light is measured over a prescribed time and temporal variation of the intensity of the scattered light is below that which is prescribed, then there is an evaluation that the measured scattered light is not producing interference. Moreover, if scattered light is measured over a prescribed time and the temporal variation of the intensity of the scattered light is equal to or greater than that which is prescribed, then there is an evaluation that the measured scattered light is producing constructive interference. Furthermore, if, for example, scattered light peaks are measured multiple times within a prescribed time interval, then there is an evaluation that the measured scattered light is producing destructive interference.

The present disclosure enables the provision of a particle detecting device and particle detecting method wherein particles can be detected accurately.

BRIEF DESCRIPTIONS OF THE DRAWINGS

DETAILED DESCRIPTION

Examples of the present disclosure will be described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

EXAMPLE

Figure 1:
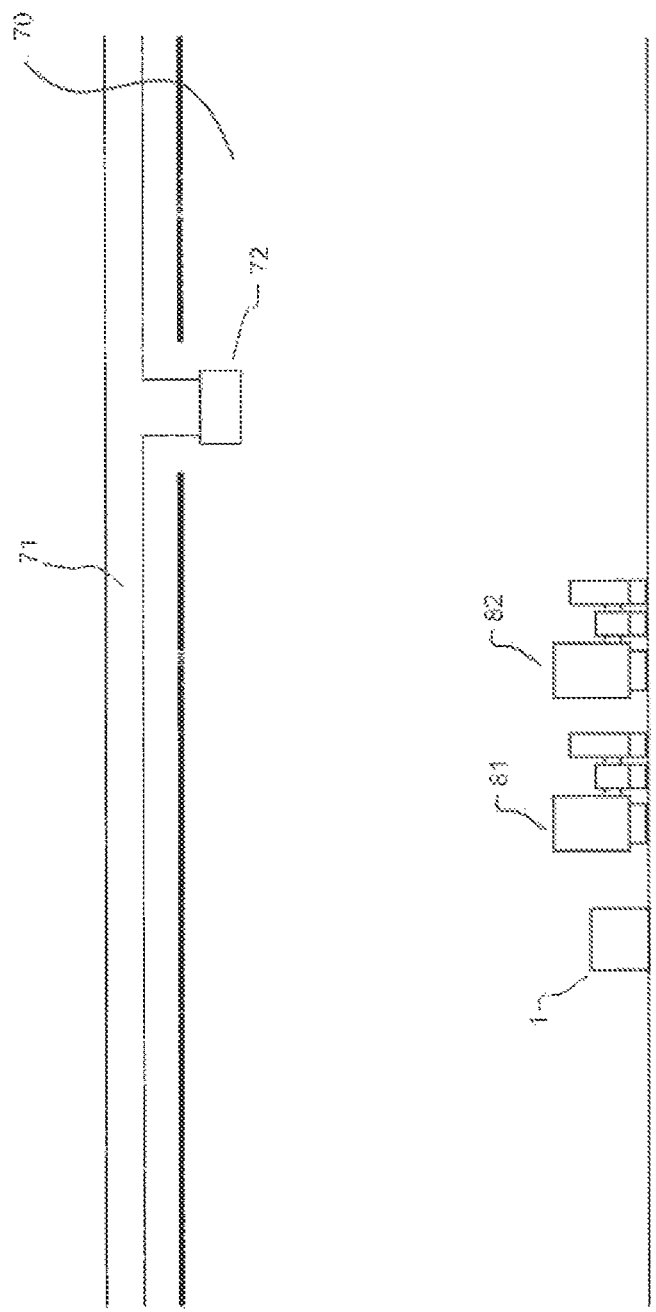
FIG. 1 is a schematic diagram of a clean room set forth in Example according to the present invention.

As illustrated in FIG. 1, a particle detecting device 1 according to the present example is disposed in, for example, a clean room 70. In the clean room 70, clean air is blown in through a duct 71 and through a blowing opening 72 having an ultrahigh performance air filter such as a HEPA filter (High Efficiency Particulate Air Filter) or ULPA filter (Ultra Low Penetration Air Filter), or the like.

Manufacturing lines 81 and 82 are arranged inside of the clean room 70. The manufacturing lines 81 and 82 are manufacturing lines, for, for example, precision instruments, electronic components, or semiconductor devices. Conversely, the manufacturing lines 81 and 82 may be manufacturing lines for foodstuffs, beverages, or pharmaceuticals. For example, in the manufacturing lines 81 and 82, an infusion liquid may be filled into an intravenous infusion device or a hypodermic. Conversely, the manufacturing lines 81 and 82 may manufacture oral medications or Chinese herb medications. On the other hand, the manufacturing lines 81 and 82 may fill containers with a vitamin drink or beer.

The manufacturing lines 81 and 82 normally are controlled so that microorganism particles and non-microorganism particles, and the like, are not dispersed into the air within the clean room 70. However, manufacturing lines 81 and 82, for some reason, are sources that produce microorganism particles and non-microorganism particles that become airborne in the clean room 70. Moreover, factors other than the manufacturing lines 81 and 82 also disperse microorganism particles and non-microorganism particles into the air of the clean room 70.

Examples of microorganism particles that may become airborne in the clean room 70 include microbes. Examples of such microbes include Gram-negative bacteria, Gram-positive bacteria, and fungi such as mold spores. *Escherichia coli*, for example, can be listed as an example of a Gram-negative bacterium. *Staphylococcus epidermidis, Bacillus atrophaeus, Micrococcus lylae*, and *Corynebacterium afermentans* can be listed as examples of Gram-positive bacteria. *Aspergillus niger* can be listed as an example of a fungus such as a mold spore. However, the microorganism particles that may become airborne in the clean room 70 are not limited to these specific examples. Examples of non-microorganism particles that may become airborne in the clean room 70 include splashed chemical substances, pharmaceuticals, or foodstuffs, along with dust, dirt, grime, and the like.

When a particle is illuminated with light, Mie scattered light, for example, is produced at the particle. Moreover, if a microorganism particle is illuminated with light, the nicotinamide adenine dinucleotide (NADH) and the flavins, and the like, that are included in microorganism particle produce fluorescent light. The wavelength of the fluorescence that derives from NADH is in the neighborhood of 480 nm. Moreover, the wavelength of the fluorescence that derives from flavins is in the neighborhood of 530 nm. Moreover, non-microorganism fluorescent particles that fall off of a gown, made from polyester, for example, that has been cleaned will emit fluorescence when illuminated with light. Moreover, polystyrene particles also emit fluorescence, and then fade. Note that "fluorescent light" includes autofluorescent light. In the below, both microorganism particles and non-microorganism fluorescent particles will be referred to as "fluorescent particles."

Figure 2:
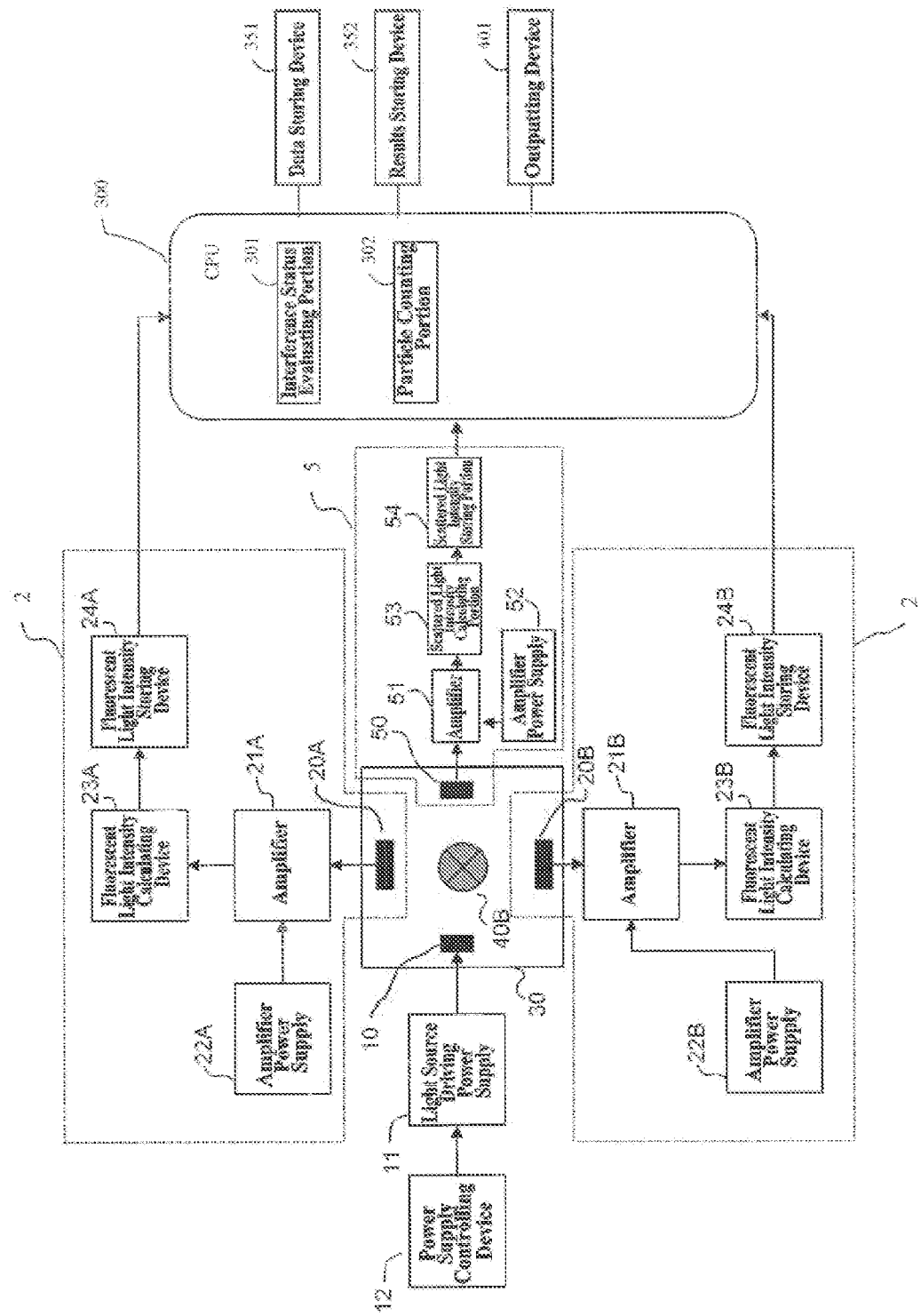
FIG. 2 is a schematic diagram of a particle detecting device as set forth in the Example according to the present invention.
Figure 3:
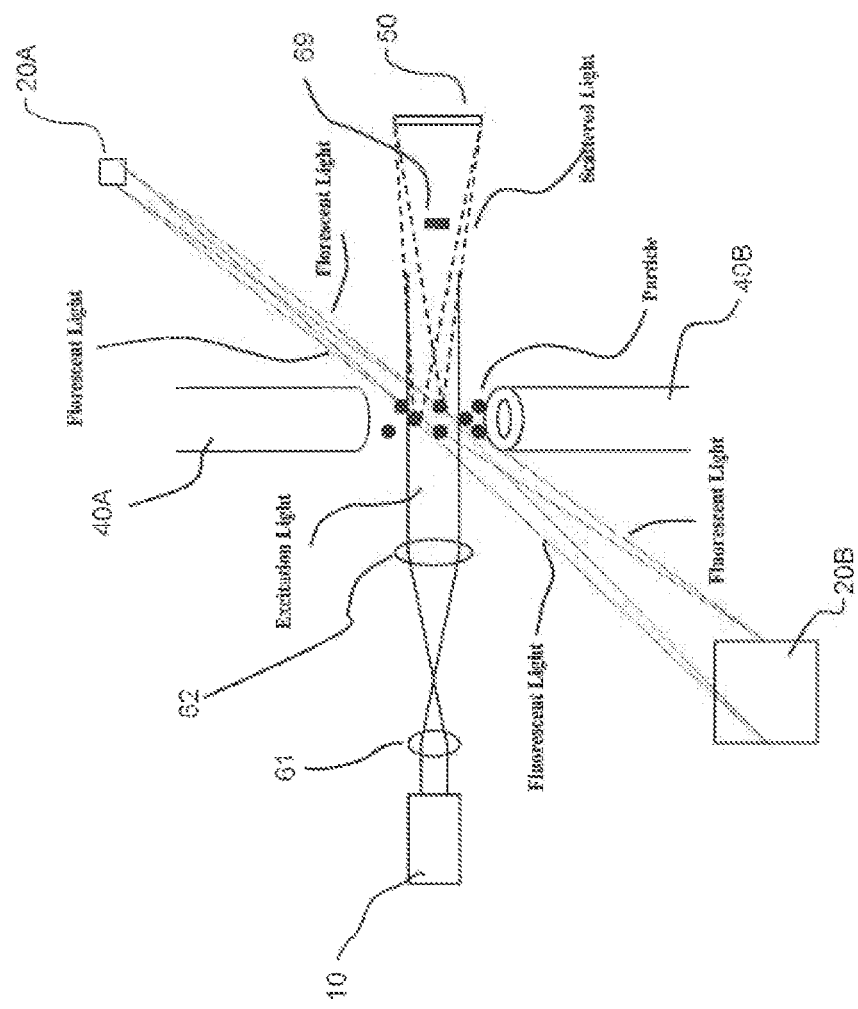
FIG. 3 is a schematic diagram of an optics system for a particle detecting device as set forth in the Example according to the present invention.

Here, as illustrated in FIG. 2 and FIG. 3, a particle detecting device 1 includes a light source 10 for directing an excitation beam into a fluid that contains a plurality of particles, a fluorescence measuring instrument 2 for measuring, at at least two different wavelengths, fluorescent light that is produced in the region that is illuminated by the excitation beam, and a scattered light measuring instrument 5 for measuring the scattered light that is produced in the region that is illuminated by the excitation beam. The fluorescence measuring instrument 2 and the scattered light measuring instrument 5 are connected electrically to a central calculating processing device (CPU) 300. The CPU 300 includes an interference status evaluating portion 301, for evaluating whether the measured scattered light is producing constructive interference and whether it is producing destructive interference, and a particle counting portion 302 for counting a plurality of particles in accordance with the interference status of the measured scattered light and for counting fluorescent particles that are subject to detection, from among the plurality of particles, based on a wavelength of fluorescent measured.

While, in the Example, the explanation will be for an example wherein the fluid that is subject to inspection is air, examples of the present invention are not limited thereto, but rather the fluid that is subject to inspection may be a liquid.

The light source 10, the fluorescence measuring instrument 2, and the scattered light measuring instrument 5 are provided in a frame 30. A light source driving power supply 11, for supplying electric power to the light source 10, is connected to the light source 10. A power supply controlling device 12, for controlling the electric power that is supplied to the light source 10, is connected to the light source driving power supply 11. The particle detecting device 1 further includes a first suction device for drawing the air, into the frame 30 that is illustrated in FIG. 2, from within the clean room 70, illustrated in FIG. 1. The air that is drawn in by the first suction device is expelled from the tip end of a nozzle 40A of the flow path, shown in FIG. 3 within the frame 30. The air that is emitted from the tip end of the nozzle 40A is drawn in, through a nozzle 40B, by a second section device that is disposed within the frame 30, facing the tip end of the nozzle 40A.

Through a light source 10 emits through, converting lenses 61 and 62, for example, an excitation beam of a wide wavelength band towards the gas flow of the air that is expelled from the tip end of the nozzle 40A and drawn into the second suction device from the nozzle 40B. A laser, a light-emitting diode (LED), a halogen lamp, a xenon lamp, or the like, may be used for the light source 10. The wavelength of the excitation beam is, for example, between 250 and 550 nm. The excitation beam may be of visible light, or of ultraviolet light. If the excitation beam is of visible light, then the wavelength of the excitation beam is within a range of, for example, 400 to 550 nm, for example, 405 nm. If the excitation beam is ultraviolet radiation, then the wavelength of the excitation beam is in a range of, for example, between 300 and 380 nm, for example, 340 nm. However, the wavelength of the excitation beam is not limited to these.

If a particle is included in the gas flow that is expelled from the nozzle 40A, Mie scattered light is produced at the particle that is illuminated by the excitation beam. The Mie scattered light that is produced by the particles is measured by the scattered light measuring instrument 5 illustrated in FIG. 2. The scattered light measuring instrument 5 is provided with a scattered light photodetecting element 50 for detecting scattered light. Note that a beam stop 69 for preventing the elimination of the excitation light directly into the scattered light photodetecting element 50 may be disposed in front of the scattered light photodetecting element 50. A photodiode, or the like, may be used for the scattered light photodetecting element 50, where, when light is received, the optical energy is converted into electrical energy. An amplifier 51, for amplifying the electric current that is produced by the scattered light photodetecting element 50 is connected to the scattered light photodetecting element 50. An amplifier power supply 52, for supplying electric power to the amplifier 51, is connected to the amplifier 51. Furthermore, a scattered light intensity calculating device 53, for receiving the electric current that has been amplified by the amplifier 51, to calculate the intensity of the scattered light that has been received by the scattered light photodetecting element 50, is connected to the amplifier 51. A scattered light intensity storing device 54, for storing the intensity of the scattered light, calculated by the scattered light intensity calculating device 53, is connected to the scattered light intensity calculating device 53.

Figure 4:
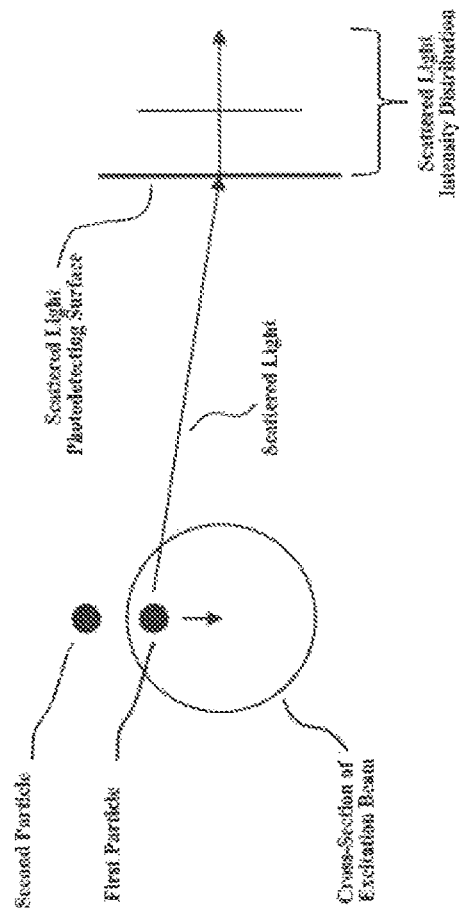
FIG. 4 is a schematic diagram illustrating the positional relationship between the beam cross-section of the excitation light and a particle in relation to the Example according to the present disclosure.
Figure 5:
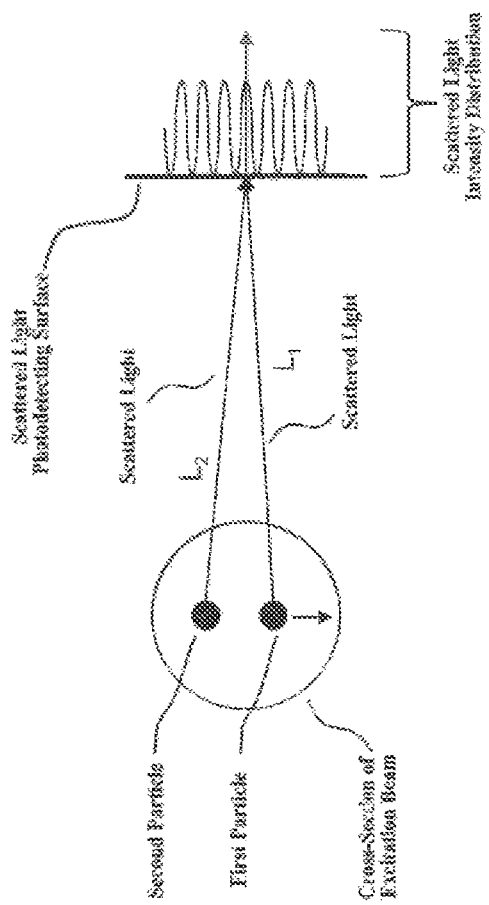
FIG. 5 is a schematic diagram illustrating the positional relationship between the beam cross-section of the excitation light and a particle in relation to the Example according to the present disclosure.
Figure 6:
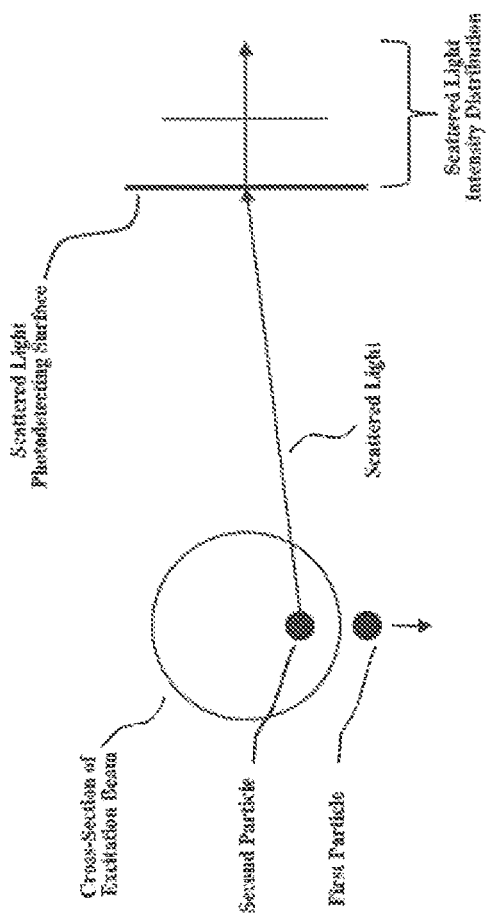
FIG. 6 is a schematic diagram illustrating the positional relationship between the beam cross-section of the excitation light and a particle in relation to the Example according to the present disclosure.

As illustrated in FIG. 4, when a first and a second particle are carried in a gas flow and the first particle enters into the cross-section of the excitation beam, scattered light is produced by the first particle, and is detected by a photosensitive surface of the scattered light photodetecting element 50. Additionally, if, as illustrated in FIG. 5, the first and second particles both enter into the cross-section of the excitation beam, scattered light will be produced by both the first and the second particles, to be detected by the photosensitive surface of the scattered light photodetecting element 50. If here both the first and the second particles exist within an interference area of the excitation beam, then the scattered light produced by the first particle and the scattered light produced by the second particle will interfere depending on the difference in the optical paths between the optical path length L1 from the first particle to the photosensitive surface of the scattered light photodetecting element 50 and the optical path length L2 from the second particle to the photosensitive surface of the scattered light photodetecting element 50. Thereafter, when the first particle exits the beam cross-section of the excitation beam, as illustrated in FIG. 6, scattered light will be produced by the second particle alone, to be detected by the scattered light photodetecting element 50.

Note that if the light source 10 is a unitary coherent light source, such as a laser, then the susceptibility to interference of the excitation beam will be high, and the interference area will be large. If the light source 10 is an incoherent light source, such as an LED, a halogen lamp, a xenon lamp, or the like, then the susceptibility to interference in the excitation beam will be low, and the interference area will be small. However, regardless of whether the light source 10 is a coherent light source or an incoherent light source, in either case there will be interference between the scattered light produced by the first particle and the scattered light produced by the second particle when both the first and second particles are within the interference area of the excitation beam.

Figure 7:
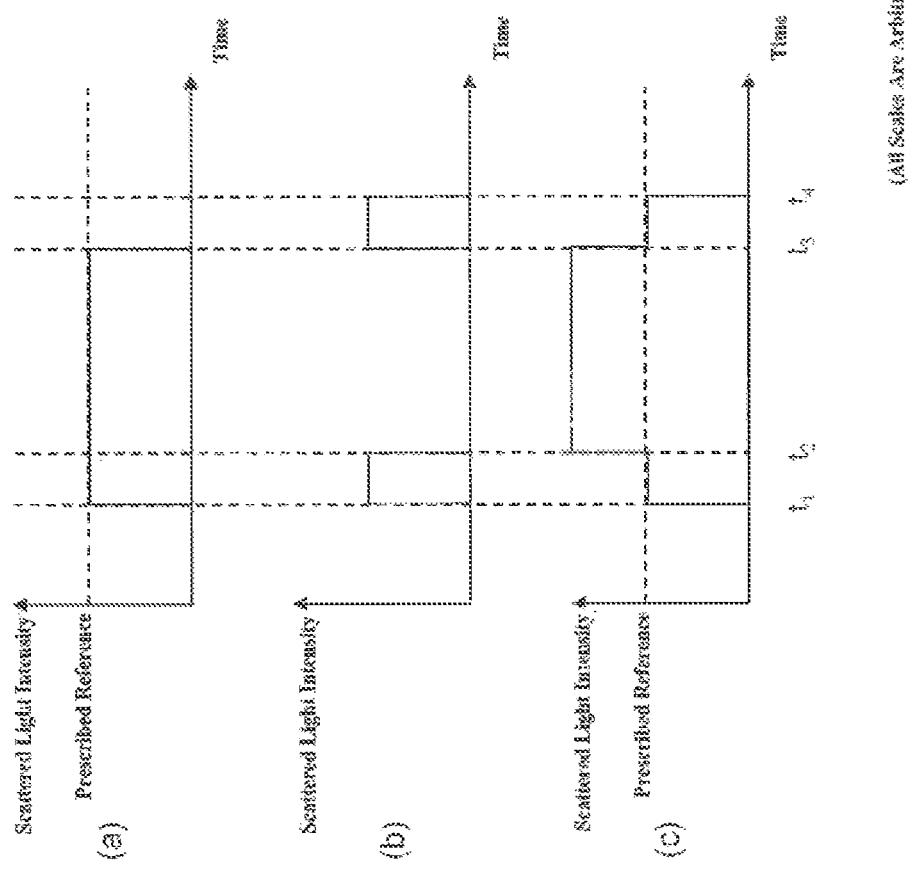
FIG. 7 is a graph illustrating schematically changes in time of the received light intensities for scattered light in relation to the Example according to the present disclosure.

FIG. 7 (a) illustrates the temporal variation in the scattered light intensity detected by the scattered light photodetecting element 50 when only a single particle passes through the cross-section of an excitation beam in a case wherein the optical intensity of the excitation beam is uniform across the cross-section thereof. FIG. 7 (b) illustrates the temporal variation of the intensity of the scattered light that is detected by the scattered light photodetecting element 50 when two particles pass through the cross-section of the excitation beam wherein the difference in the optical path lengths between and optical path length L1 between the first particle and the photosensitive surface of the scattered light photodetecting element 50 and the optical path length L2 between the second particle and the photosensitive surface of the scattered light photodetecting element 50 corresponds to, for example, an odd multiple of the half wavelengths of the scattered light so that the scattered lights interfere destructively with each other. FIG. 7 (c) illustrates the temporal variation in the intensity of the scattered light that is detected by the scattered light photodetecting element 50 when two particles pass through the cross-section of the excitation beam and the difference in the optical path lengths corresponds, for example, to an integer multiple of the wavelength of the scattered light so that the scattered lights interfere constructively with each other.

In FIG. 7 (b) and FIG. 7 (c), during the interval from time t1 to t2, only the first particle is passing through the cross-section of the excitation beam. In the interval from time t2 to t3, the first and second particles are passing through the cross-section of the excitation beam. At time t3, the first particle exits the cross-section of the excitation beam, and during the interval from time t3 to t4, only the second particle is passing through the cross-section of the excitation beam.

In FIG. 7 (b), destructive interference is produced between the scattered lights that are produced by the first and second particles, during the interval from time t2 through t3, and thus the intensity of the scattered light detected by the scattered light photodetecting element 50 is essentially zero. Because of this, in intervals within a prescribed time, within the interval from time t1 to time t4, peaks for the scattered light will be measured twice. Note that although there may be cases wherein the intensity of the scattered light that is detected will not be perfectly zero, even when destructive interference occurs, because of false signals due to stray random electric noise or stray random electromagnetic emission lines, still it is possible to suppress the effects of false signals through, for example, canceling any calculated optical intensity that is less than a standard value.

In FIG. 7(c), the intensity of the scattered light that is detected by the scattered light photodetecting element 50 increases due to the occurrence of constructive interference between the scattered lights produced by the first and second particles, during the interval from time t2 through t3. Because of this, the temporal variation of the intensity of the scattered light, which is continuously measured without interruption across the prescribed time during the interval from time t1 through time t4, will be above a prescribed standard for the scattered light. Note that this prescribed standard for the scattered light is, for example, a threshold value that is able to discriminate between the temporal variation of the intensity of scattered light produced by a single particle and the temporal variation in the intensity when produced through constructive interference of the scattered light that is produced by a plurality of particles, acquired by checking both in advance.

If a microorganism particle, such as a bacterium, or the like, is included in the gas flow that is expelled from the nozzle 40A, illustrated in FIG. 3, scattered light is produced at the microorganism particle, and, additionally, the microorganism particle that is illuminated by the excitation beam will emit fluorescence. Moreover, even in a case wherein a non-microorganism fluorescent particle, such as a polyester particle, is included in the gas flow that is expelled from the nozzle 40A, scattered light will be produced at the non-microorganism fluorescent particle, and also the non-microorganism fluorescent particle that is illuminated by the excitation beam will emit fluorescence. Note that with fluorescent light, there is no interference between the fluorescent lights because of the phase of the excitation beam being random.

The fluorescence measuring instrument 2, illustrated in FIG. 2, measures the fluorescence that is produced by the microorganism particles and the non-microorganism fluorescent particles. The fluorescence measuring instrument 2 includes: a fluorescent light detecting element 20A for detecting light in the fluorescent band at a first wavelength, and a fluorescent light detecting element 20B for detecting light of a fluorescent band at a second wavelength that is different from the first wavelength. Note that the "first wavelength" may have a band. The same is true for the second wavelength. A photodiode or a photoelectron multiplier tube, or the like, may used for the fluorescent light detecting element 20A and the fluorescent light detecting element 20B, where, when light is received, the optical energy is converted into electrical energy.

An amplifier 21A, for amplifying the electric current that is produced by the fluorescent light detecting element 20A is connected to the fluorescent light detecting element 20A. An amplifier power supply 22A, for supplying electric power to the amplifier 21A, is connected to the amplifier 21A. Furthermore, a fluorescent light intensity calculating device 23A, for receiving the electric current that has been amplified by the amplifier 21A, to calculate the intensity of the fluorescence that has been received by the fluorescent light detecting element 20A, is connected to the amplifier 21A. A fluorescent light intensity storing device 24A, for storing the intensity of the fluorescence, calculated by the fluorescent light intensity calculating device 23A, is connected to the fluorescent light intensity calculating device 23A.

An amplifier 21B, for amplifying the electric current that is produced by the fluorescent light detecting element 20B is connected to the fluorescent light detecting element 20B. An amplifier power supply 22B, for supplying electric power to the amplifier 21B, is connected to the amplifier 21B. Furthermore, a fluorescent light intensity calculating device 23B, for receiving the electric current that has been amplified by the amplifier 21B, to calculate the intensity of the fluorescence that has been received by the fluorescent light detecting element 20B, is connected to the amplifier 21B. A fluorescent light intensity storing device 24B, for storing the intensity of the fluorescence, calculated by the fluorescent light intensity calculating device 23B, is connected to the fluorescent light intensity calculating device 23B. Note that while in FIG. 2 an example is shown wherein the fluorescence measuring instrument 2 is provided with the two fluorescent light detecting elements 20A and 20B, the fluorescence measuring instrument 2 may be provided with a greater number of photodetecting elements instead, to measure the intensities of light at a plurality of other wavelengths in the fluorescent band as well.

Figure 8:
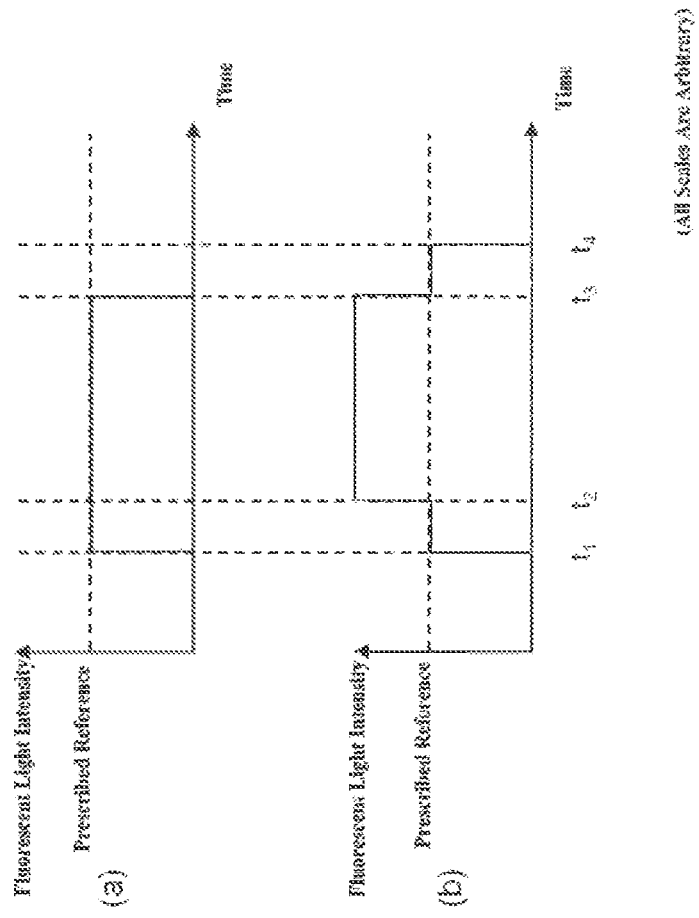
FIG. 8 is a graph illustrating schematically changes in time of the received light intensities for fluorescent light in relation to the Example according to the present disclosure.

FIG. 8 (a) illustrates the temporal variation in the fluorescent light intensity detected by the fluorescent light detecting element 20A and/or 20B when only a single fluorescent particle passes through the cross-section of an excitation beam in a case wherein the optical intensity of the excitation beam is uniform across the cross-section thereof. FIG. 8 (b) illustrates the temporal variation in the fluorescent light intensity detected by the fluorescent light detecting element 20A and/or 20B when two single fluorescent particles pass through the cross-section of the excitation beam. In FIG. 8 (b), first, at time t1, the first fluorescent particle enters into the cross-section of the excitation beam alone, and during the interval from time t1 to t2, only the first fluorescent particle is passing through the cross-section of the excitation beam. At time t2, the second fluorescent particle also enters into the cross-section of the excitation beam, and during the interval from time t2 to t3, both the first and second fluorescent particles are passing through the cross-section of the excitation beam. At time t3, the first fluorescent particle exits the cross-section of the excitation beam, and during the interval from time t3 to t4, only the second fluorescent particle is passing through the cross-section of the excitation beam. At time t4, the second fluorescent particle exits the cross-section of the excitation beam.

In the interval from time t2 through t3, there is no interference between the fluorescence emitted from the first and second fluorescent particles, and thus the respective fluorescent intensities add together. Because of this, the temporal variation of the intensity of the fluorescent light, which is continuously measured without interruption across the prescribed time during the interval from time t1 through time t4, will be above a prescribed standard for the fluorescent light. Note that this prescribed standard for the fluorescent light is, for example, a threshold value that is able to discriminate between the temporal variation of the intensity of fluorescent light produced by a single fluorescent particle and the temporal variation in the intensity of the fluorescent light that is produced by a plurality of fluorescent particles, acquired by checking both in advance.

Figure 9:
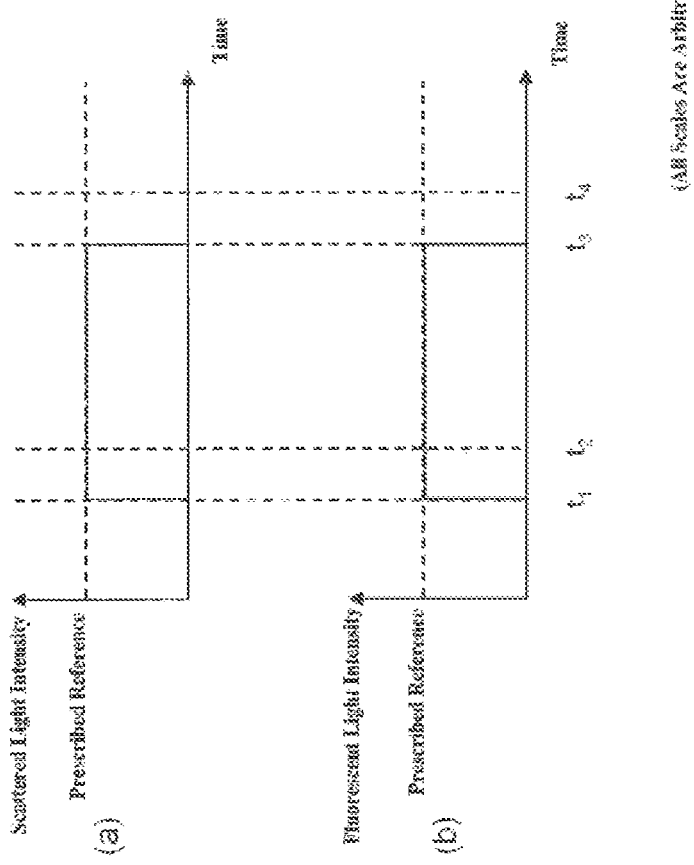
FIG. 9 is a graph illustrating schematically changes in time of the received light intensities for scattered light and fluorescent light when a single fluorescent particle passes through the beam cross section of the excitation light in relation to the Example according to the present disclosure.

FIGS. 9 (a) and (b) illustrate the temporal variation in the scattered light that is detected by the scattered light photodetecting element 50 and the temporal variation in the fluorescent light intensity detected by the fluorescent light detecting element 20A and/or 20B when only a single fluorescent particle passes through the cross-section of an excitation beam in a case wherein the optical intensity of the excitation beam is uniform across the cross-section thereof. In this case there is no interference, and thus, the temporal variation of the intensity of the scattered light, which is continuously measured without interruption across the prescribed time during the interval from time t1 through time t3, will be less than the prescribed standard for the scattered light. Additionally, the temporal variation of the intensity of the fluorescent light, which is continuously measured without interruption across the prescribed time during the interval from time t1 through time t3, will be less than the prescribed standard for the fluorescent light.

Additionally, the time t1 at which the measurement begins with the scattered light photodetecting element 50 detecting the scattered light is essentially the same as the time t1 at which the fluorescent light detecting element 20A and/or 20B begins measuring through detecting the fluorescent light. Furthermore, the time t3 that is the end of the measurement, when the scattered light photodetecting element 50 ceases detecting scattered light, is essentially equal to the time t3 at which the fluorescent light detecting element 20A and/or 20B ends the measurement because fluorescent light ceases to be detected. Because of this, the length of time over which the scattered light is measured and the length of time over which the fluorescent light is measured are essentially equal. Note that the clock monitoring the time over which the scattered light is measured and the clock monitoring the time over which the fluorescent light is measured will not be perfectly synchronized, due to drift in the liquid crystal oscillators of the internal clocks in the fluorescence measuring instrument 2 and the scattered light measuring instrument 5, and the like, producing error between the time over which the scattered light is measured and the time over which the fluorescent light is measured. However, discrepancies in times within a tolerance range are ignored.

Figure 10:
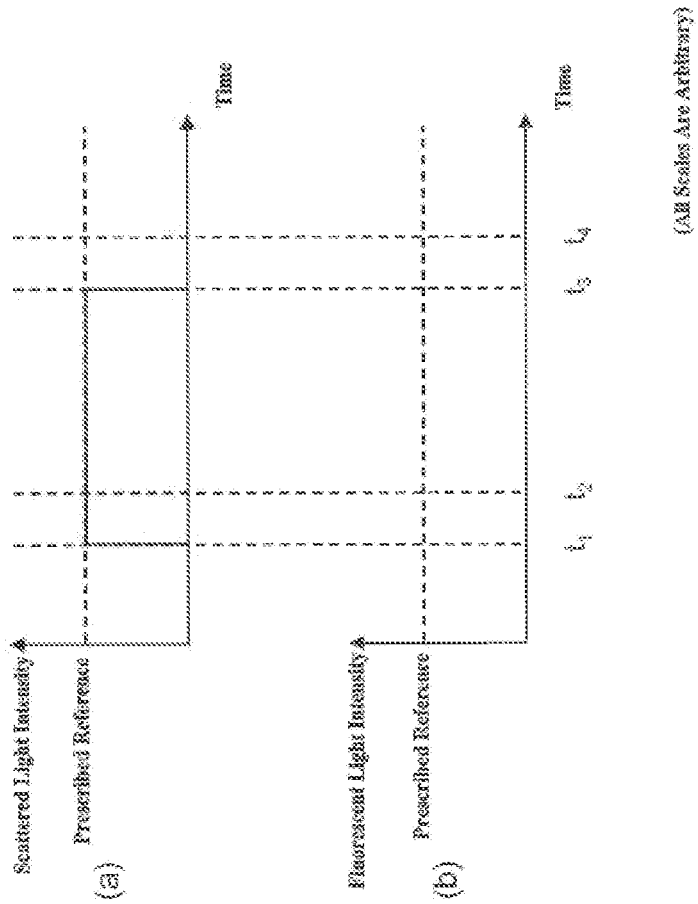
FIG. 10 is a graph illustrating schematically changes in time of the received light intensities for scattered light and fluorescent light when a single non-fluorescent particle passes through the beam cross section of the excitation light in relation to the Example according to the present disclosure.

FIGS. 10 (a) and (b) illustrate the temporal variation in the scattered light that is detected by the scattered light photodetecting element 50 and the temporal variation in the fluorescent light intensity detected by the fluorescent light detecting element 20A or 20B when only a single non-fluorescent particle passes through the cross-section of the excitation beam. In this case as well there is no interference, and thus, the temporal variation of the intensity of the scattered light, which is continuously measured without interruption across the prescribed time during the interval from time t1 through time t3, will be less than the prescribed standard for the scattered light. Note that the non-fluorescent particles do not emit fluorescent light, so during the interval that the photodetecting element 50 is detecting scattered light, the intensity of the light detected by the fluorescent light detecting element 20A or 20B remains at essentially zero.

Figure 11:
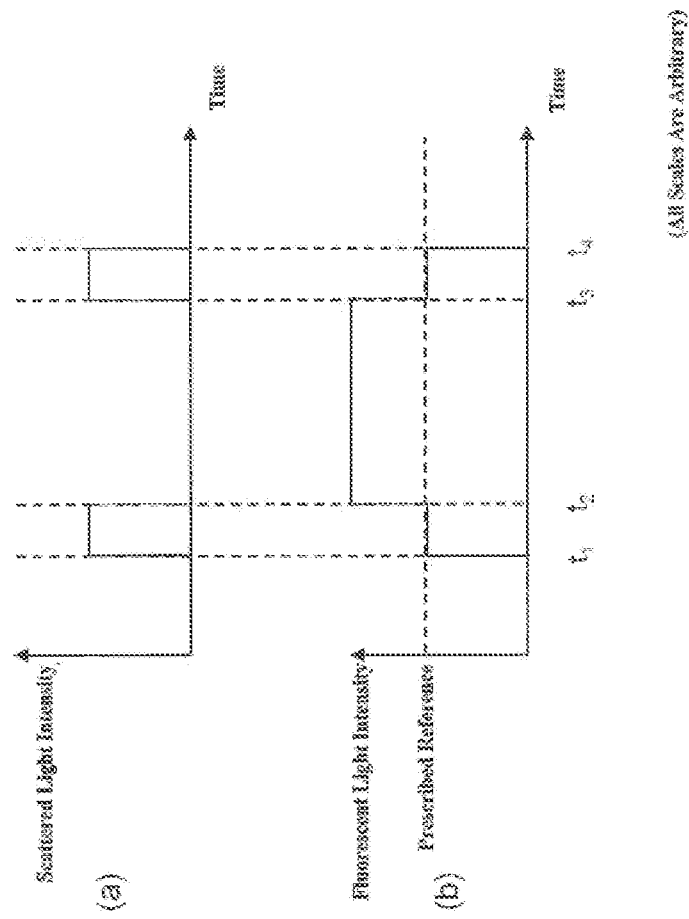
FIG. 11 is a graph illustrating schematically changes in time of the received light intensities for scattered light and fluorescent light when two fluorescent particles pass through the beam cross section of the excitation light, producing destructive interference, in relation to the Example according to the present disclosure.

FIGS. 11 (a) and (b) illustrate the temporal variation in the scattered light that is detected by the scattered light photodetecting element 50 and the temporal variation in the fluorescent light intensity detected by the fluorescent light detecting element 20A and/or 20B when two fluorescent particles pass through the cross-section of the excitation beam and destructive interference is produced between the scattered lights that are produced by the two fluorescent particles. In this case, peaks for the scattered light will be measured twice in intervals within a prescribed time, within the interval from time t1 to time t4, due to the destructive interference. Additionally, because in the interval from time t2 to time t3, the fluorescent lights that are produced from the two fluorescent particles add together, so that the temporal variation of the intensity of the fluorescent light, which is continuously measured without interruption across the prescribed time during the interval from time t1 through time t4, will be equal to or greater than the prescribed standard for the fluorescent light. Additionally, the time t1 at which the measurement begins with the scattered light photodetecting element 50 detecting the scattered light is essentially the same as the time t1 at which the fluorescent light detecting element 20A and/or 20B begins measuring through detecting the fluorescent light. Furthermore, the time t4 that is the end of the measurement, when the scattered light photodetecting element 50 ceases detecting scattered light, is essentially equal to the time t4 at which the fluorescent light detecting element 20A and/or 20B ends the measurement because fluorescent light ceases to be detected.

Figure 12:
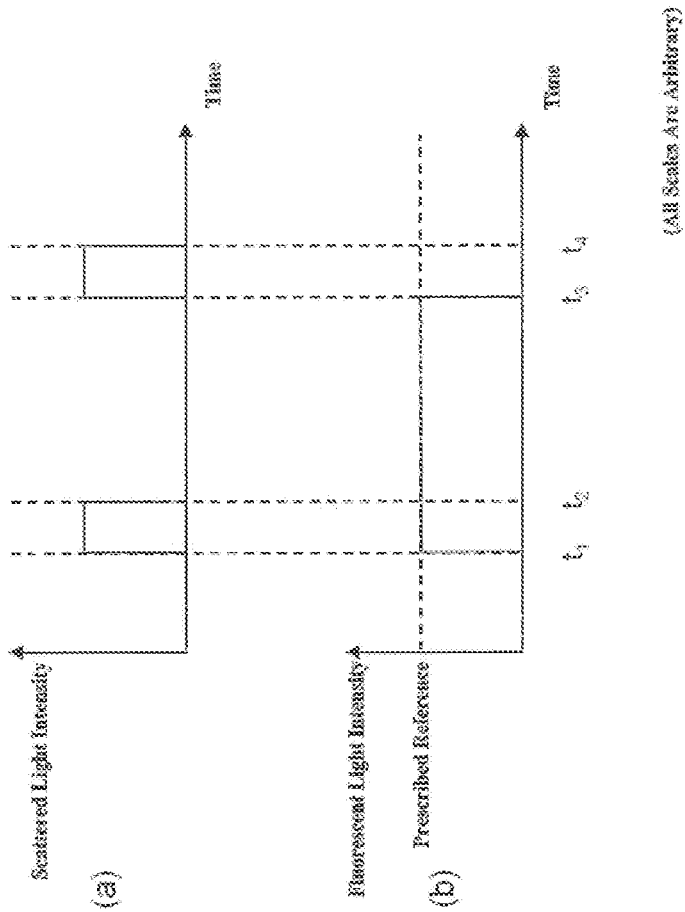
FIG. 12 is a graph illustrating schematically changes in time of the received light intensities for scattered light and fluorescent light when, following a single fluorescent particle, a single non-fluorescent particle passes through the beam cross section of the excitation light, producing destructive interference, in relation to the Example according to the present disclosure.

FIGS. 12 (a) and (b) illustrate the temporal variation in the scattered light that is detected by the scattered light photodetecting element 50 and the temporal variation in the fluorescent light intensity detected by the fluorescent light detecting element 20A and/or 20B when one non-fluorescent particle following one fluorescent particle pass through the cross-section of the excitation beam and destructive interference is produced between the scattered light that is produced by the fluorescent particle and the scattered light that is produced by the non-fluorescent particle. In this case, peaks for the scattered light will be measured twice in intervals within a prescribed time, within the interval from time t1 to time t4, due to the destructive interference. Additionally, the time t1 at which the measurement begins with the scattered light photodetecting element 50 detecting the scattered light is essentially the same as the time t1 at which the fluorescent light detecting element 20A and/or 20B begins measuring through detecting the fluorescent light. However, because the non-fluorescent particle that exits the cross-section of the excitation beam after the fluorescent particle does not emit fluorescent light, the time t4 that is the end of the measurement, when the scattered light photodetecting element 50 ceases detecting scattered light, is different from the time t3 at which the fluorescent light detecting element 20A and/or 20B ends the measurement because fluorescent light ceases to be detected.

Figure 13:
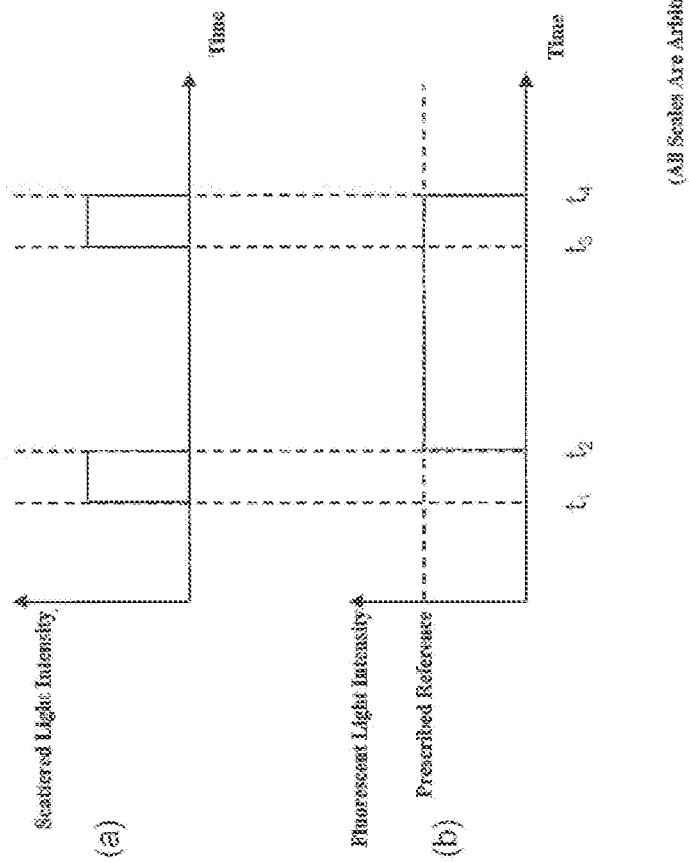
FIG. 13 is a graph illustrating schematically changes in time of the received light intensities for scattered light and fluorescent light when, following a single non-fluorescent particle, a single fluorescent particle passes through the beam cross section of the excitation light, producing destructive interference, in relation to the Example according to the present disclosure.

FIGS. 13 (a) and (b) illustrate the temporal variation in the scattered light that is detected by the scattered light photodetecting element 50 and the temporal variation in the fluorescent light intensity detected by the fluorescent light detecting element 20A and/or 20B when one fluorescent particle following one non-fluorescent particle pass through the cross-section of the excitation beam and destructive interference is produced between the scattered light that is produced by the non-fluorescent particle and the scattered light that is produced by the fluorescent particle. In this case, peaks for the scattered light will be measured twice in intervals within a prescribed time, within the interval from time t1 to time t4, due to the destructive interference. Additionally, the time t1 at which the measurement begins with the scattered light photodetecting element 50 detecting the scattered light is different from the time t2 at which the fluorescent light detecting element 20A and/or 20B begins measuring through detecting the fluorescent light. However, because the fluorescent particle that exits the cross-section of the excitation beam after the non-fluorescent particle emits fluorescent light until time t4, the time t4 that is the end of the measurement, when the scattered light photodetecting element 50 ceases detecting scattered light, is essentially the same as the time t4 at which the fluorescent light detecting element 20A and/or 20B ends the measurement because fluorescent light ceases to be detected.

Figure 14:
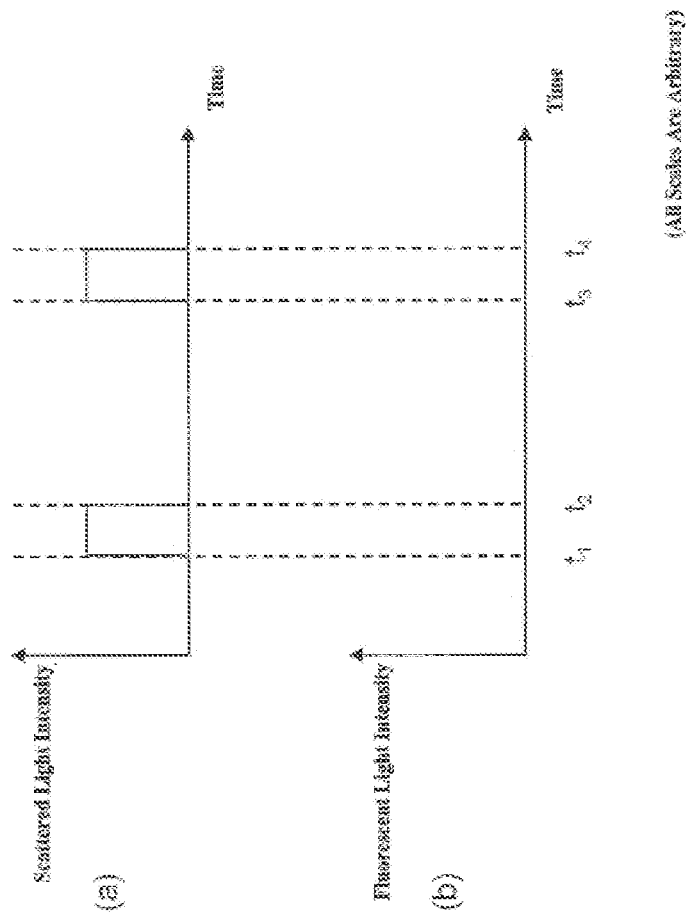
FIG. 14 is a graph illustrating schematically changes in time of the received light intensities for scattered light and fluorescent light when two non-fluorescent particles pass through the beam cross section of the excitation light, producing destructive interference, in relation to the Example according to the present disclosure.

FIGS. 14 (a) and (b) illustrate the temporal variation in the scattered light that is detected by the scattered light photodetecting element 50 and the temporal variation in the fluorescent light intensity detected by the fluorescent light detecting element 20A or 20B when two non-fluorescent particles pass through the cross-section of the excitation beam and destructive interference is produced between the scattered lights that are produced by the two non-fluorescent particles. In this case, peaks for the scattered light will be measured twice in intervals within a prescribed time, within the interval from time t1 to time t4, due to the destructive interference. Moreover, because the two non-fluorescent particles do not emit fluorescent light, during the interval that the photodetecting element 50 is detecting scattered light fluorescent light is also not measured, so the intensity of the light detected by the fluorescent light detecting element 20A or 20B remains at essentially zero.

Figure 15:
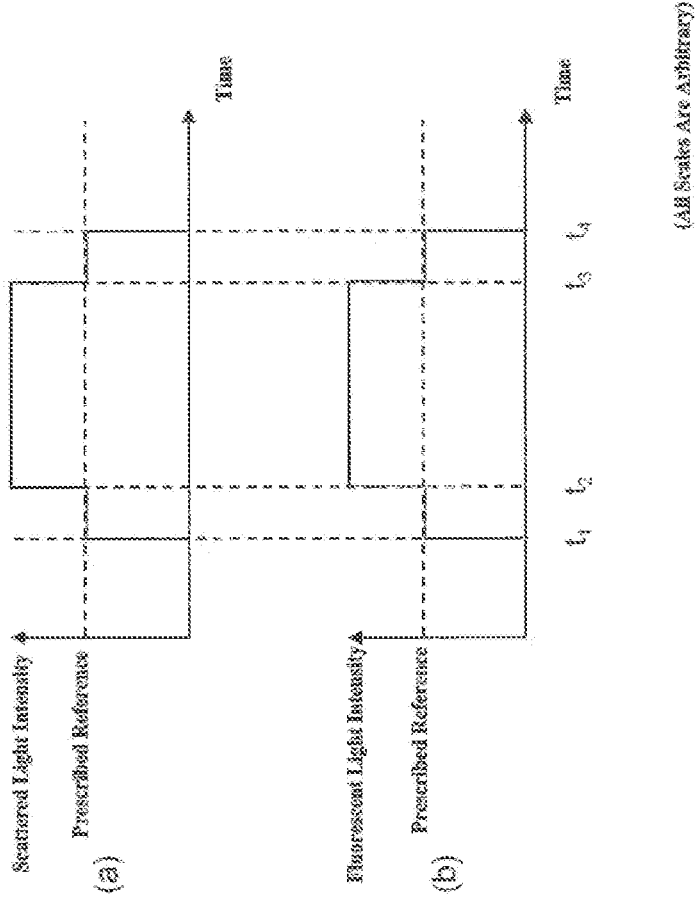
FIG. 15 is a graph illustrating schematically changes in time of the received light intensities for scattered light and fluorescent light when two fluorescent particles pass through the beam cross section of the excitation light, producing constructive interference, in relation to the Example according to the present disclosure.

FIGS. 15 (a) and (b) illustrate the temporal variation in the scattered light that is detected by the scattered light photodetecting element 50 and the temporal variation in the fluorescent light intensity detected by the fluorescent light detecting element 20A and/or 20B when two fluorescent particles pass through the cross-section of the excitation beam and constructive interference is produced between the scattered lights that are produced by the two fluorescent particles. Because of the constructive interference in this case, the temporal variation of the intensity of the scattered light, which is continuously measured without interruption across the prescribed time during the interval from time t1 through time t4, will be above a prescribed standard for the scattered light. Additionally, because in the interval from time t2 to time t3, the fluorescent lights that are produced from the two fluorescent particles add together, so that the temporal variation of the intensity of the fluorescent light, which is continuously measured without interruption across the prescribed time during the interval from time t1 through time t4, will be equal to or greater than the prescribed standard for the fluorescent light. Additionally, the time t1 at which the measurement begins with the scattered light photodetecting element 50 detecting the scattered light is essentially the same as the time t1 at which the fluorescent light detecting element 20A and/or 20B begins measuring through detecting the fluorescent light. Furthermore, the time t4 that is the end of the measurement, when the scattered light photodetecting element 50 ceases detecting scattered light, is essentially equal to the time t4 at which the fluorescent light detecting element 20A and/or 20B ends the measurement because fluorescent light ceases to be detected.

Because of this, the times over which the scattered light in the fluorescent light are measured will be essentially equal.

Figure 16:
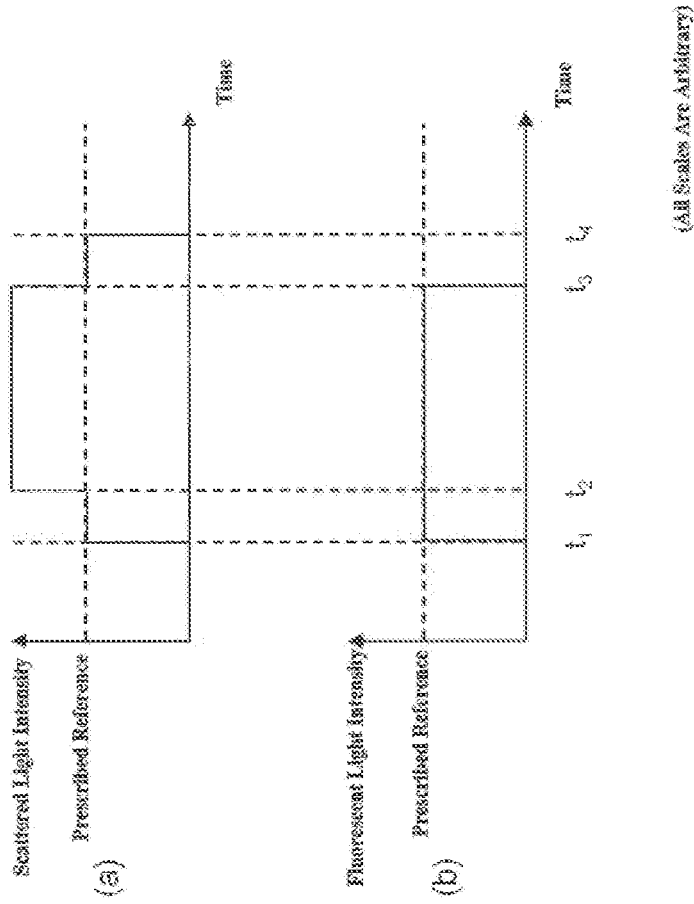
FIG. 16 is a graph illustrating schematically changes in time of the received light intensities for scattered light and fluorescent light when, following a single fluorescent particle, a single non-fluorescent particle passes through the beam cross section of the excitation light, producing constructive interference, in relation to the Example according to the present disclosure.

FIGS. 16 (a) and (b) illustrate the temporal variation in the scattered light that is detected by the scattered light photodetecting element 50 and the temporal variation in the fluorescent light intensity detected by the fluorescent light detecting element 20A and/or 20B when one non-fluorescent particle following one fluorescent particle pass through the cross-section of the excitation beam and constructive interference is produced between the scattered light that is produced by the fluorescent particle and the scattered light that is produced by the non-fluorescent particle. Because of the constructive interference in this case, the temporal variation of the intensity of the scattered light, which is continuously measured without interruption across the prescribed time during the interval from time t1 through time t4, will be above a prescribed standard for the scattered light. Additionally, the time t1 at which the measurement begins with the scattered light photodetecting element 50 detecting the scattered light is essentially the same as the time t1 at which the fluorescent light detecting element 20A and/or 20B begins measuring through detecting the fluorescent light. However, because the non-fluorescent particle that exits the cross-section of the excitation beam after the fluorescent particle does not emit fluorescent light, the time t4 that is the end of the measurement, when the scattered light photodetecting element 50 ceases detecting scattered light, is different from the time t3 at which the fluorescent light detecting element 20A and/or 20B ends the measurement because fluorescent light ceases to be detected. Because of this, the times over which the scattered light in the fluorescent light are measured will be different.

Figure 17:
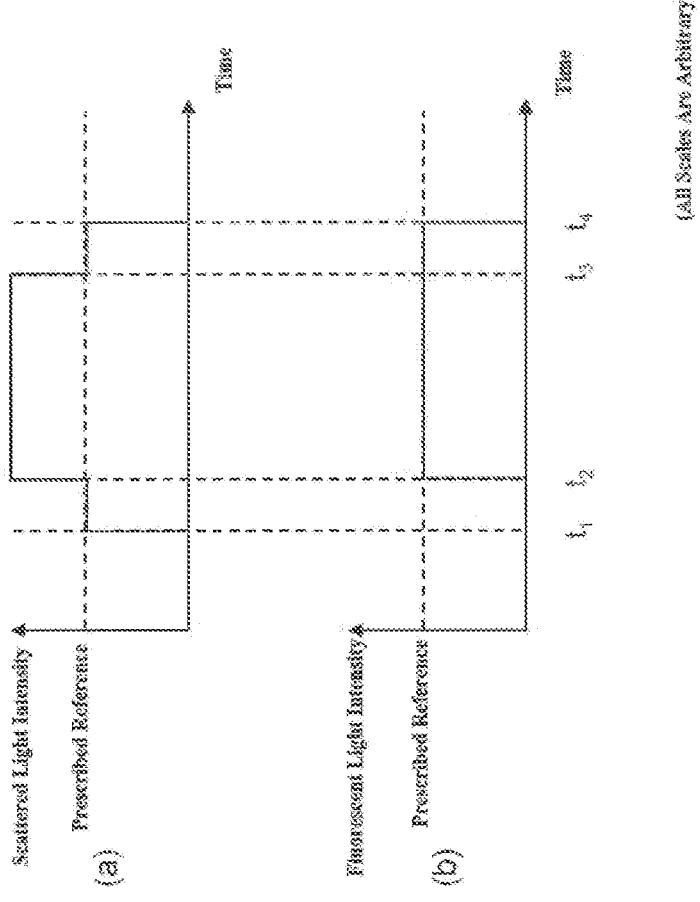
FIG. 17 is a graph illustrating schematically changes in time of the received light intensities for scattered light and fluorescent light when, following a non-single fluorescent particle, a single fluorescent particle passes through the beam cross section of the excitation light, producing constructive interference, in relation to the Example according to the present disclosure.

FIGS. 17 (a) and (b) illustrate the temporal variation in the scattered light that is detected by the scattered light photodetecting element 50 and the temporal variation in the fluorescent light intensity detected by the fluorescent light detecting element 20A and/or 20B when one fluorescent particle following one non-fluorescent particle pass through the cross-section of the excitation beam and constructive interference is produced between the scattered light that is produced by the non-fluorescent particle and the scattered light that is produced by the fluorescent particle. Because of the constructive interference in this case, the temporal variation of the intensity of the scattered light, which is continuously measured without interruption across the prescribed time during the interval from time t1 through time t4, will be above a prescribed standard for the scattered light. Additionally, the time t1 at which the measurement begins with the scattered light photodetecting element 50 detecting the scattered light is different from the time t2 at which the fluorescent light detecting element 20A and/or 20B begins measuring through detecting the fluorescent light. Because of this, the times over which the scattered light in the fluorescent light are measured will be different. However, because the fluorescent particle that exits the cross-section of the excitation beam after the non-fluorescent particle emits fluorescent light until time t4, the time t4 that is the end of the measurement, when the scattered light photodetecting element 50 ceases detecting scattered light, is essentially the same as the time t4 at which the fluorescent light detecting element 20A and/or 20B ends the measurement because fluorescent light ceases to be detected.

Figure 18:
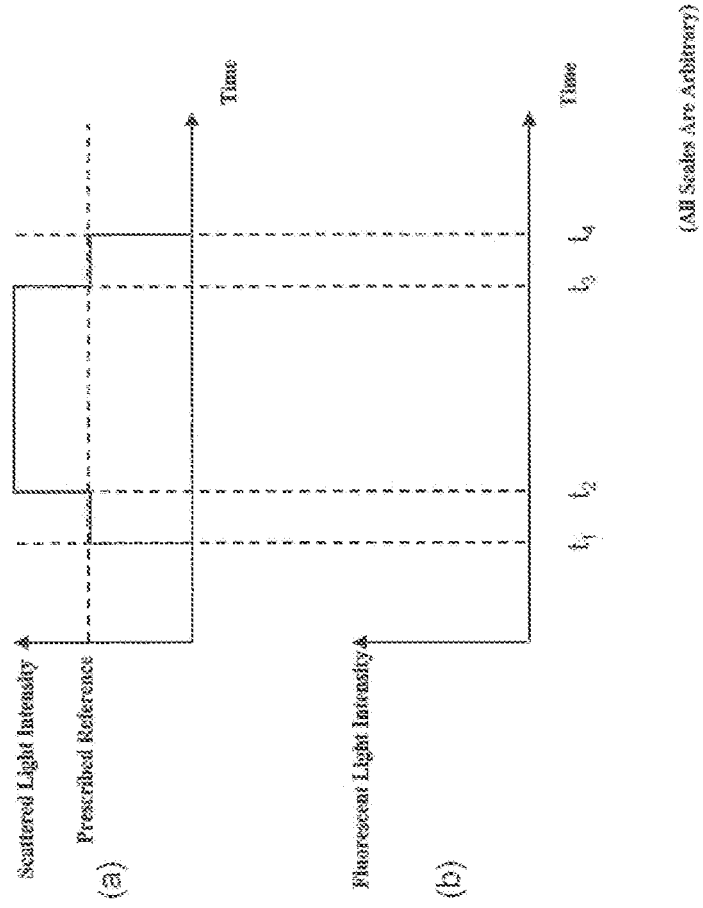
FIG. 18 is a graph illustrating schematically changes in time of the received light intensities for scattered light and fluorescent light when two non-fluorescent particles pass through the beam cross section of the excitation light, producing constructive interference, in relation to the Example according to the present disclosure.

FIGS. 18 (a) and (b) illustrate the temporal variation in the scattered light that is detected by the scattered light photodetecting element 50 and the temporal variation in the fluorescent light intensity detected by the fluorescent light detecting element 20A or 20B when two non-fluorescent particles pass through the cross-section of the excitation beam and constructive interference is produced between the scattered lights that are produced by the two non-fluorescent particles. Because of the constructive interference in this case, the temporal variation of the intensity of the scattered light, which is continuously measured without interruption across the prescribed time during the interval from time t1 through time t4, will be above a prescribed standard for the scattered light. Moreover, because the two non-fluorescent particles do not emit fluorescent light, during the interval that the photodetecting element 50 is detecting scattered light fluorescent light is also not measured, so the intensity of the light detected by the fluorescent light detecting element 20A or 20B remains at essentially zero.

The interference status evaluating portion 301 and the particle counting portion 302, illustrated in FIG. 2, read out the temporal variation of the intensity of the scattered light from the scattered light intensity storing device 54. Additionally, the interference status evaluating portion 301 and the particle counting portion 302 read out the temporal variations of the intensities of the fluorescent light from the fluorescent light intensity storing devices 24A and 24B. A data storing device 351 is connected to the CPU 300. The data storing device 351 stores a prescribed standard for the scattered light, and the wavelength of the fluorescence that is emitted from the fluorescent particles that are subject to detection. The prescribed standard for the scattered light is adjusted as appropriate in response to the sizes, refractive indices, and reflectivities of the particles that are to be detected, and in accordance with the size of the scattered light photodetecting element 50, and the like. The interference status evaluating portion 301 and the particle counting portion 302 read out the prescribed standard, for the scattered light, from the data storing device 351, and the wavelength of the fluorescence that is emitted from the fluorescent particles that are subject to detection.

The interference status evaluating portion 301 measures the scattered light continuously, without interruption, over the prescribed time interval, as illustrated in FIG. 9 and FIG. 10, and if the temporal variation of the intensity of the scattered light is less than the prescribed standard for the scattered light, evaluates that a single particle has passed the cross-section of the excitation beam and that no interference was produced within the scattered light that was measured. If, as illustrated in any of the FIG. 11 through FIG. 14, peaks in the scattered light are measured multiple times during the interval within the prescribed time, then the interference status evaluating portion 301 evaluates that at least two particles have passed through the cross-section of the excitation beam, and that destructive interference was produced in the scattered light that was measured. Furthermore, as illustrated in any of FIG. 15 through FIG. 18, if scattered light is measured continuously without interruption across the prescribed time and the temporal variation of the intensity of the scattered light is equal to or greater than the prescribed standard for the scattered light, then the interference status evaluating portion 301 evaluates that at least two particles have passed through the cross-section of the excitation beam and that constructive interference was produced in the scattered light that was measured.

If, as illustrated in FIG. 2, the interference status evaluating portion 301 evaluates that a single particle has passed through the cross-section of the excitation beam, the particle counting portion 302 checks whether or not fluorescent light was measured. If, as illustrated in FIG. 9, fluorescent light was measured, then the particle counting portion 302, illustrated in FIG. 2, evaluates that the single particle that has passed through the cross-section of the excitation beam was a fluorescent particle, and records, in the results recording device 352 that is connected to the CPU 300, that a single fluorescent particle was detected.

Moreover, the particle counting portion 302 evaluates whether or not the wavelength of the fluorescent light that has been measured is the same as the wavelength of the fluorescent light that is emitted by a fluorescent particle that is subject to detection. If the wavelength of the fluorescent light that has been measured is the same as the wavelength of the fluorescent light that is emitted by a fluorescent particle that is subject to detection, then the particle counting portion 302 evaluates that the single particle that has been detected is a fluorescent particle that is subject to detection, and records, in the results recording device 352 that the single fluorescent particle that has been detected is a fluorescent particle that is subject to detection. Moreover, if the wavelength of the fluorescent light that has been measured is different from the wavelength of the fluorescent light that is emitted by a fluorescent particle that is subject to detection, then the particle counting portion 302 evaluates that the single particle that has been detected is not a fluorescent particle that is subject to detection, and records, in the results recording device 352 that the single fluorescent particle that has been detected is not a fluorescent particle that is subject to detection.

Moreover, if, as illustrated in FIG. 10, no fluorescent light was measured, then the particle counting portion 302, illustrated in FIG. 2, evaluates that the single particle that passed through the cross-section of the excitation beam was a non-fluorescent particle, and records, in the results recording device 352, that a single non-fluorescent particle was detected.

If, as illustrated in FIG. 2, the interference status evaluating portion 301 evaluates that, for example, two particles have passed through the cross-section of the excitation beam, and that the measured scattered light has produced destructive interference, the particle counting portion 302 checks whether or not fluorescent light was measured. Moreover, if, as illustrated in FIG. 11 through FIG. 13, fluorescent light was measured, then the particle counting portion 302, illustrated in FIG. 2, evaluates that at least one of the two particles that passed through the cross-section of the excitation beam was a fluorescent particle.

Moreover, if, as illustrated in FIG. 11, the time at which the measurement of the fluorescent light began is essentially equal to the time at which the measurement of the first scattered light began, and the time at which the measurement of the fluorescent light ended was essentially equal to the time at which the measurement of the last scattered light ended, then the particle counting portion 302, illustrated in FIG. 2, evaluates that both of the two particles that passed through the beam cross-section of the excitation beam were fluorescent particles, and stores, in the results recording device 352, that two fluorescent particles were detected. Moreover, if, as illustrated in FIG. 13, the time at which the measurement of the fluorescent light began is different from the time at which the measurement of the first scattered line began, or, as illustrated in FIG. 12, the time at which the measurement of the fluorescent light ended is different from the end of measurement of the scattered light, then the particle counting portion 302, illustrated in FIG. 2, evaluates that one of the two particles that passed through the cross-section of the excitation beam was a fluorescent particle and the other particle was a non-fluorescent particle, and records, in the results recording device 352, that there was a single fluorescent particle and a single non-fluorescent particle. Moreover, the particle counting portion 302 evaluates whether or not the wavelength of the fluorescent light that has been measured is the same as the wavelength of the fluorescent light that is emitted by a fluorescent particle that is subject to detection, and, in response to the evaluation, records in the results recording device 352 whether or not the fluorescent particle that has been detected is a fluorescent particle that is subject to detection.

If, as illustrated in FIG. 14, no fluorescent light was measured, then the particle counting portion 302, illustrated in FIG. 2, evaluates that both particles that passed through the cross-section of the excitation beam were non-fluorescent particles, and records, in the results recording device 352, that two non-fluorescent particles were detected.

If, as illustrated in FIG. 2, the interference status evaluating portion 301 evaluates that, for example, two particles have passed through the cross-section of constructive excitation beam, and that the measured scattered light has produced destructive interference, the particle counting portion 302 checks whether or not fluorescent light was measured. Moreover, if, as illustrated in FIG. 15 through FIG. 17, fluorescent light was measured, then the particle counting portion 302, illustrated in FIG. 2, evaluates that at least one of the two particles that passed through the cross-section of the excitation beam was a fluorescent particle.

Moreover, if, as illustrated in FIG. 15, the lengths of time measured for the scattered light and for the fluorescent light were essentially equal, then the particle counting portion 302, illustrated in FIG. 2, evaluates that both particles that passed through the cross-section of the excitation beam were fluorescent particles, and records, in the results recording device 352, that two fluorescent particles were detected. Moreover, if, as illustrated in FIG. 16 and FIG. 17, the lengths of time measured for the scattered light and for the fluorescent light were different, then the particle counting portion 302, illustrated in FIG. 2, evaluates that one of the two particles that passed through the cross-section of the excitation beam was a fluorescent particle and the other particle was a non-fluorescent particle, and records, in the results recording device 352, the detection of one fluorescent particle and of one non-fluorescent particle. Moreover, the particle counting portion 302 evaluates whether or not the wavelength of the fluorescent light that has been measured is the same as the wavelength of the fluorescent light that is emitted by a fluorescent particle that is subject to detection, and, in response to the evaluation, records in the results recording device 352 whether or not the fluorescent particle that has been detected is a fluorescent particle that is subject to detection.

If, as illustrated in FIG. 18, no fluorescent light was measured, then the particle counting portion 302, illustrated in FIG. 2, evaluates that both particles that passed through the cross-section of the excitation beam were non-fluorescent particles, and records, in the results recording device 352, that two non-fluorescent particles were detected. Note that the results recorded in the results recording device 352, described above, may also be outputted from an outputting device 401, such as a printer, a display, or the like, connected to the CPU 300.

With the conventional particle detecting device, no thought is given to interference between the scattered lights, so that each time a scattered light is detected, the detection of a single particle is recorded. However, if, as illustrated in FIG. 15 through FIG. 18, there is constructive interference between the scattered light from a plurality of particles, scattered light is measured continuously, without interruption, over the prescribed time, and thus the number of times that scattered light has been measured will be only once. Because of this, in a conventional detecting device the record will be incorrect, with only a single particle being counted, despite, for example, two particles passing through the cross-section of the excitation beam.

In contrast, with the particle detecting device 1 according to the Example, illustrated in FIG. 2, an evaluation is performed as to whether there is constructive interference in the scattered light and whether there is destructive interference, to count a plurality of particles depending on the interference status of the scattered light. Because of this, even if there is constructive interference between the scattered lights, still the particle detecting device 1 counts a plurality of particles, enabling accurate recording. Furthermore, the particle detecting device 1 can count dividing the plurality of particles into fluorescent particles and non-fluorescent particles based on the measurement times of the scattered lights, the temporal variation within the intensities of the scattered lights, and the measurement times for the florescent lights, and the like.

Moreover, if moisture such as water vapor, nitrogen oxides ($NO_x$), including nitrogen dioxide ($NO_2$), sulfur oxides ($SO_x$), ozone gas ($O_3$), gases of aluminum oxides, aluminum alloys, glass powders, and decontaminating gases for decontaminating contamination such as *Escherichia coli*, molds, and the like, are included in the air, then organic substances in the air, which might be smaller than these particles that produce Mie scattering, may absorb the excitation light and emit light in the fluorescent band. Note that "light of the fluorescent band" is not limited to fluorescence, but rather this wavelength band includes also Raman scattered light (inelastically scattered light) that overlaps with the fluorescence.

For example, with the moisture that is illuminated by the excitation light, such as ultraviolet radiation, Raman scattered light will be produced in the vicinity of a wavelength of 460 nm, which is near to the wavelength of NADH-derived fluorescence. Moreover, when nitrogen dioxide absorbs gas, light that has shifted in the red direction is emitted, to return to the ground state. The absorption spectrum of nitrogen dioxide has a peak in the vicinity of 440 nm, and has a wide band of between 100 and 200 nm. Because of this, when, in the presence of nitrogen dioxide, an NADH-derived or flavin-derived fluorescence, which has a wavelength of 405 nm, is stimulated, then fluorescence will be stimulated in the nitrogen dioxide as well, which overlaps the absorption spectrum of the excitation beam for the NADH and the flavin. Furthermore, nitrogen dioxide is produced by a reaction between nitrogen and oxygen in the air when a material is combusted. Because of this, even if there is no nitrogen dioxide included in the air that was originally to be tested, when the particle detecting device illuminates the light with a laser beam with a high beam density, or a strong electromagnetic emission line, as the excitation beam, substances within the air may combust to produce nitrogen dioxide, where this nitrogen dioxide will emit fluorescence. In addition, carbon monoxide and ozone may react to produce nitrogen dioxide, which also emits fluorescence.

In regards to nitrogen dioxide, see Japanese Unexamined Patent Application Publication 2003-139707, Joel A. Thornton, et al., "Atmospheric NO2: In Situ Laser-Induced Fluorescence Detection at Parts-per-Trillion Mixing Ratios," Analytical Chemistry, Vol. 72, No. 3, Feb. 1, 2000, Pages 528-539, and S. A. Nizkorodov, et al., "Time-Resolved Fluorescence of NO2 in a Magnetic Field," Vol. 215, No. 6, Chemical Physics Letters, 17 Dec. 1993, Pages 662-667. For sulfur dioxide, see Japanese Unexamined Patent Application Publication 2012-86105.

Consequently, when the evaluation as to whether or not there is a fluorescent particle that is subject to detection is made based entirely on whether or not light of the fluorescent band has been detected, there may be an incorrect evaluation that there is a fluorescent particle that is subject to detection, where light in the fluorescent band that is emitted from a substance other than a fluorescent particle that is subject to detection is detected. In contrast, the particle detecting device 1 as set forth in the Example is able to prevent this false detection through evaluating whether or not the fluorescent wavelength that has been measured is the same as the wavelength of the fluorescent light that is produced by the fluorescent particle that is subject to detection, obtained in advance.

Another Example

Figure 19:
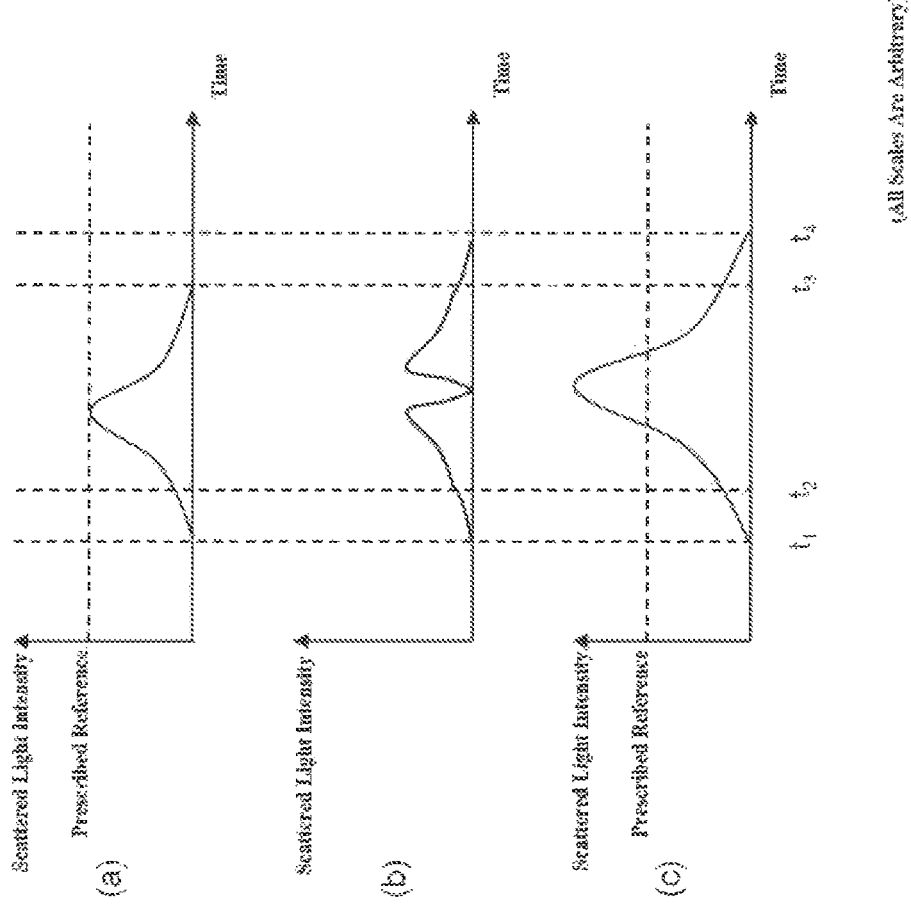
FIG. 19 is a graph illustrating schematically changes in time of the received light intensities for scattered light in relation to Another Example according to the present disclosure.

While in the Example the explanation was for a case wherein the optical intensity was uniform in the cross-section of the excitation beam, the excitation beam may be a Gaussian beam instead. FIG. 19 (*a*) shows the temporal variation in the intensity of the scattered light detected by the scattered light photodetecting element 50, illustrated in FIG. 2, when a single particle passes through the cross-section of the excitation beam when the excitation beam is a Gaussian beam. FIG. 19 (*a*) shows the temporal variation in the intensity of the scattered light detected by the scattered light photodetecting element 50, illustrated in FIG. 2, when two particles pass through the cross-section of the excitation beam and the scattered lights destructively interfere with each other. FIG. 19 (*c*) shows the temporal variation in the intensity of the scattered light detected by the scattered light photodetecting element 50, illustrated in FIG. 2, when two particles pass through the cross-section of the excitation beam and the scattered lights constructively interfere with each other.

In the case wherein there is no interference, in FIG. 19 (*a*), the temporal variation of the intensity of the scattered light, which is continuously measured without interruption across the prescribed time, will be less than the prescribed standard for the scattered light. In the case wherein there is destructive interference, in FIG. 19 (*b*), peaks for the scattered light will be measured twice within a prescribed time. In the case wherein there is constructive interference, in FIG. 19 (*c*), the temporal variation of the intensity of the scattered light, which is continuously measured without interruption across the prescribed time, will be equal to or greater than the prescribed standard for the scattered light.

Figure 20:
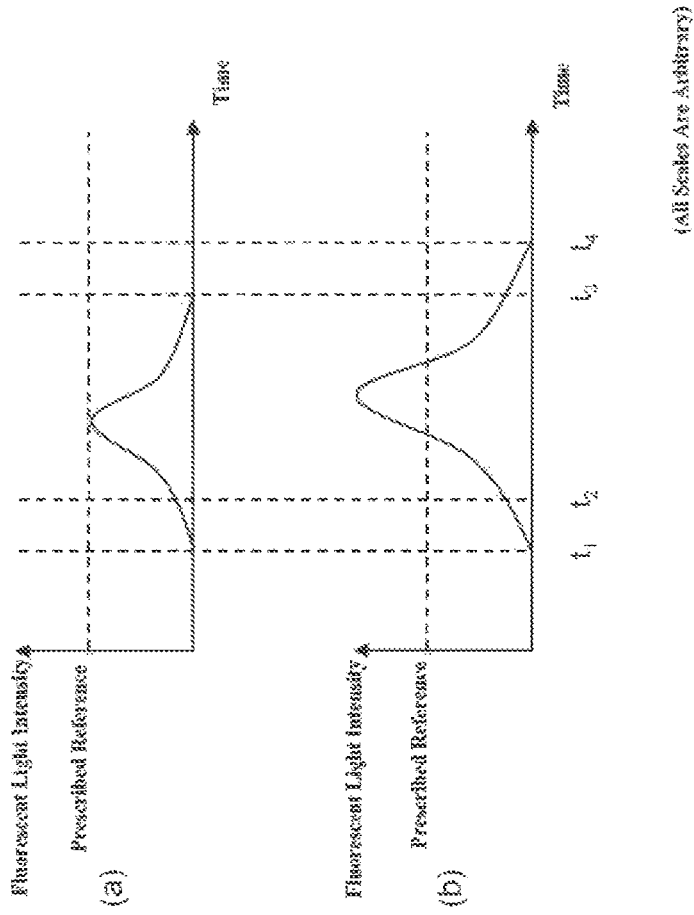
FIG. 20 is a graph illustrating schematically changes in time of the received light intensities for fluorescent light in relation to the Another Example according to the present disclosure.

FIG. 20 (*a*) illustrates the temporal variation in the fluorescent light intensity detected by the fluorescent light detecting element 20A and/or 20B when only a single fluorescent particle passes through the cross-section of an excitation beam in a case wherein the excitation beam is a Gaussian beam. FIG. 20 (*b*) illustrates the temporal variation in the fluorescent light intensity detected by the fluorescent light detecting element 20A and/or 20B when two single fluorescent particles pass through the cross-section of the excitation beam. In FIG. 20 (*b*), there is no interference between the fluorescence emitted from the first and second fluorescent particles, and thus the respective fluorescent intensities add together.

Figure 21:
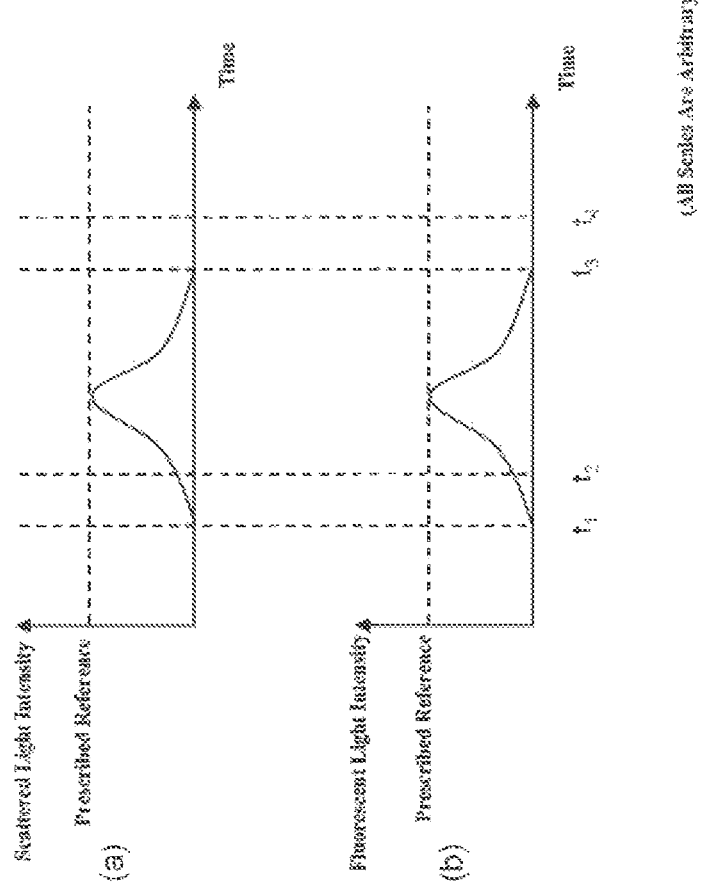
FIG. 21 is a graph illustrating schematically changes in time of the received light intensities for scattered light and fluorescent light when a single fluorescent particle passes through the beam cross section of the excitation light in relation to the Another Example according to the present disclosure.

FIGS. 21 (*a*) and (*b*) illustrate the temporal variation in the scattered light that is detected by the scattered light photodetecting element 50 and the temporal variation in the fluorescent light intensity detected by the fluorescent light detecting element 20A and/or 20B when only a single fluorescent particle passes through the cross-section of the excitation beam in a case wherein the excitation beam is a Gaussian beam. In this case the temporal variation of the intensity of the scattered light, which is continuously measured without interruption across the prescribed time, will be less than the prescribed standard for the scattered light. Additionally, the temporal variation of the intensity of the fluorescent light, which is continuously measured without interruption across the prescribed time, will be less than the prescribed standard for the fluorescent light. Additionally, the time t1 at which the measurement begins with the scattered light photodetecting element 50 detecting the scattered light is essentially the same as the time t1 at which the fluorescent light detecting element 20A and/or 20B begins measuring through detecting the fluorescent light. Furthermore, the time t3 that is the end of the measurement, when the scattered light photodetecting element 50 ceases detecting scattered light, is essentially equal to the time t3 at which the fluorescent light detecting element 20A and/or 20B ends the measurement because fluorescent light ceases to be detected.

Figure 22:
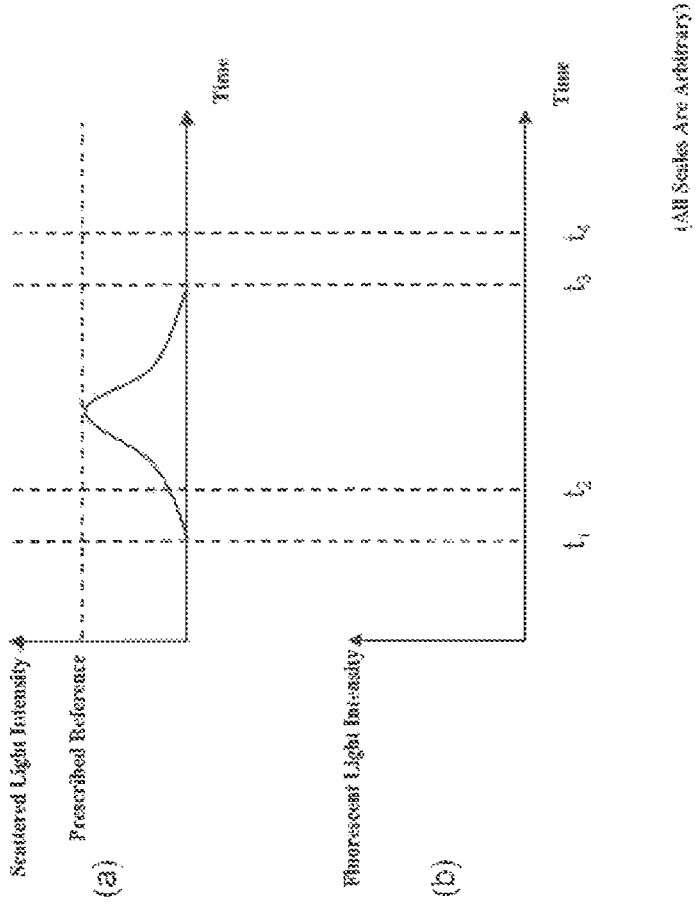
FIG. 22 is a graph illustrating schematically changes in time of the received light intensities for scattered light and fluorescent light when a single non-fluorescent particle passes through the beam cross section of the excitation light in relation to the Another Example according to the present disclosure.

FIGS. 22 (a) and (b) illustrate the temporal variation in the scattered light that is detected by the scattered light photodetecting element 50 and the temporal variation in the fluorescent light intensity detected by the fluorescent light detecting element 20A or 20B when only a single non-fluorescent particle passes through the cross-section of the excitation beam. In this case, the intensity of the light detected by the fluorescent light detecting element 20A or 20B remains at essentially zero during the interval that the photodetecting element 50 is detecting scattered light.

Figure 23:
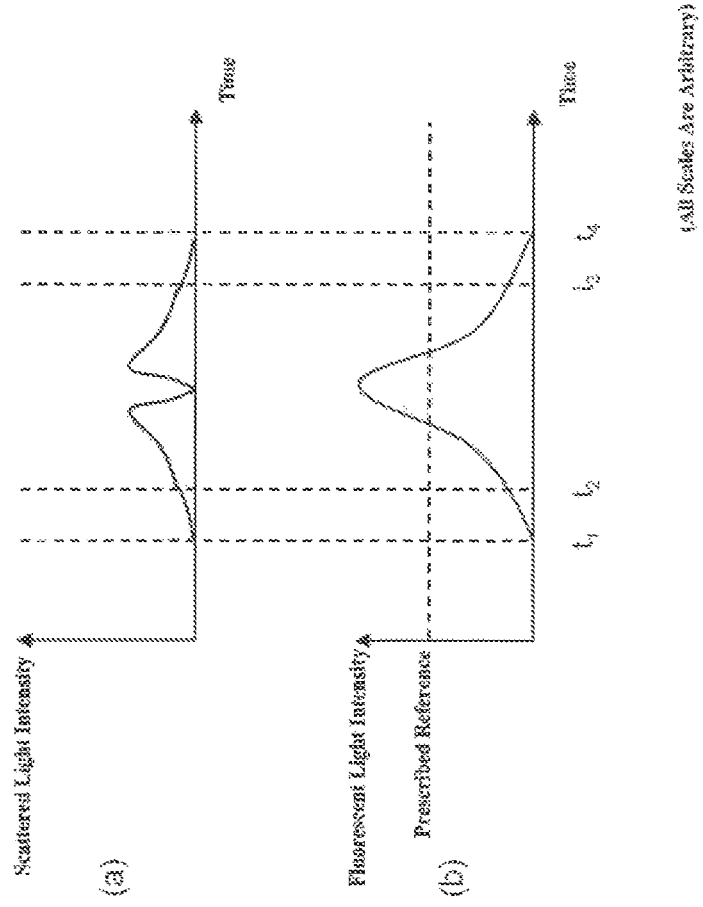
FIG. 23 is a graph illustrating schematically changes in time of the received light intensities for scattered light and fluorescent light when two fluorescent particles pass through the beam cross section of the excitation light, producing destructive interference, in relation to the Another Example according to the present disclosure.

FIGS. 23 (a) and (b) illustrate the temporal variation in the scattered light that is detected by the scattered light photodetecting element 50 and the temporal variation in the fluorescent light intensity detected by the fluorescent light detecting element 20A and/or 20B when two fluorescent particles pass through the cross-section of the excitation beam and destructive interference is produced between the scattered lights that are produced by the two fluorescent particles. In this case, the scattered light peaks will be measured twice within a prescribed time interval. Additionally, the temporal variation of the intensity of the fluorescent light, which is continuously measured without interruption across the prescribed time, will be equal to or greater than the prescribed standard for the fluorescent light. Additionally, the time t1 at which the measurement begins with the scattered light photodetecting element 50 detecting the scattered light is essentially the same as the time t1 at which the fluorescent light detecting element 20A and/or 20B begins measuring through detecting the fluorescent light. Furthermore, the time t4 that is the end of the measurement, when the scattered light photodetecting element 50 ceases detecting scattered light, is essentially equal to the time t4 at which the fluorescent light detecting element 20A and/or 20B ends the measurement because fluorescent light ceases to be detected.

Figure 24:
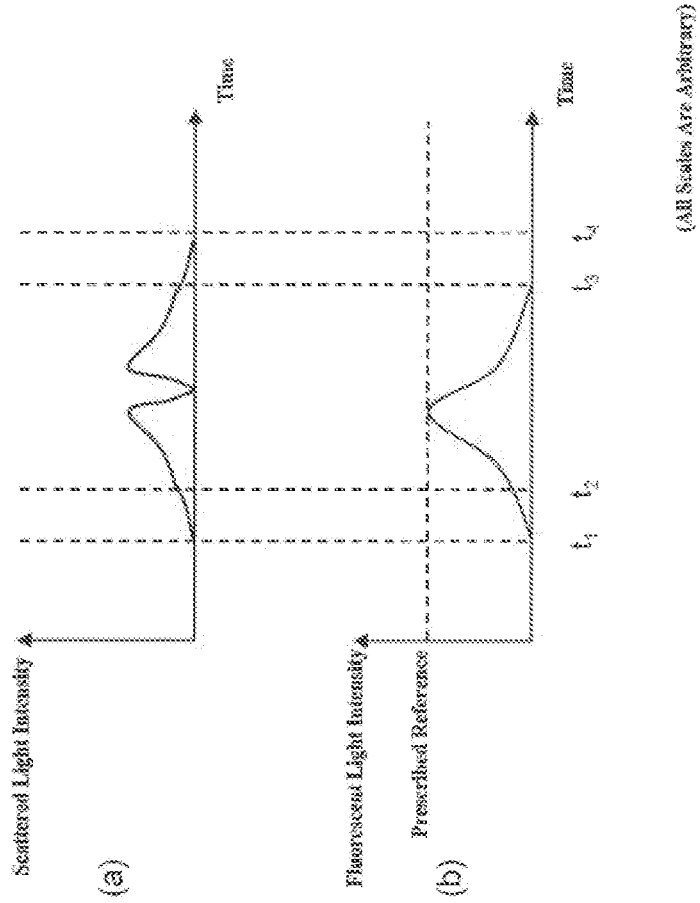
FIG. 24 is a graph illustrating schematically changes in time of the received light intensities for scattered light and fluorescent light when, following a single fluorescent particle, a single non-fluorescent particle passes through the beam cross section of the excitation light, producing destructive interference, in relation to the Another Example according to the present disclosure.

FIGS. 24 (a) and (b) illustrate the temporal variation in the scattered light that is detected by the scattered light photodetecting element 50 and the temporal variation in the fluorescent light intensity detected by the fluorescent light detecting element 20A and/or 20B when one non-fluorescent particle following one fluorescent particle pass through the cross-section of the excitation beam and destructive interference is produced between the scattered light that is produced by the fluorescent particle and the scattered light that is produced by the non-fluorescent particle. In this case, the scattered light peaks will be measured twice within a prescribed time interval. Additionally, the time t4 at which the measurement ends when the scattered light photodetecting element 50 ceases to detect scattered light is different from time the t3 when the measurement by the fluorescent light detecting element 20A and/or 20B is completed because it ceases to detect fluorescent light.

Figure 25:
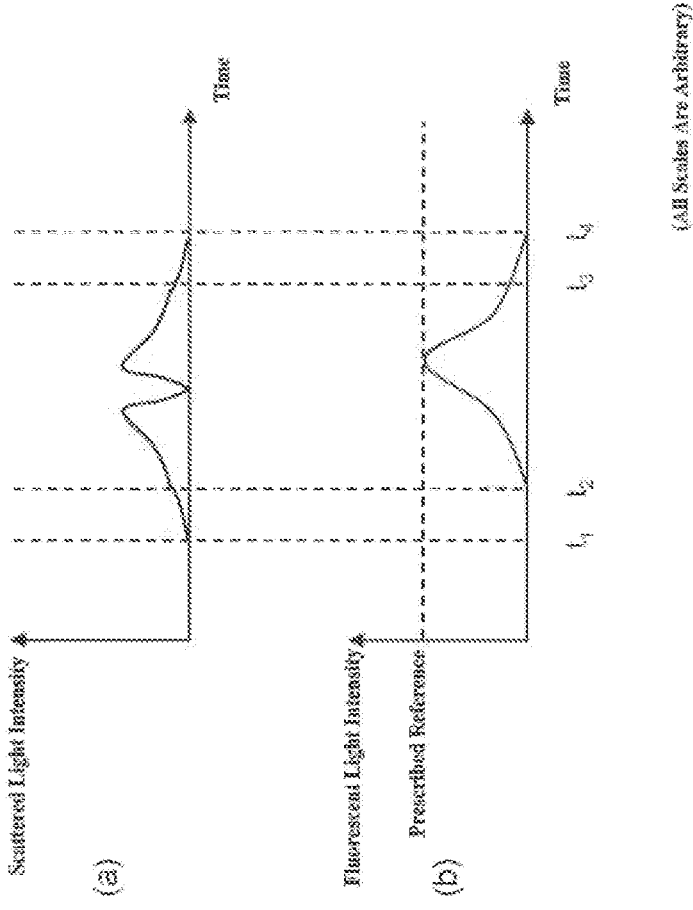
FIG. 25 is a graph illustrating schematically changes in time of the received light intensities for scattered light and fluorescent light when, following a single non-fluorescent particle, a single fluorescent particle passes through the beam cross section of the excitation light, producing destructive interference, in relation to the Another Example according to the present disclosure.

FIGS. 25 (a) and (b) illustrate the temporal variation in the scattered light that is detected by the scattered light photodetecting element 50 and the temporal variation in the fluorescent light intensity detected by the fluorescent light detecting element 20A and/or 20B when one fluorescent particle following one non-fluorescent particle pass through the cross-section of the excitation beam and destructive interference is produced between the scattered light that is produced by the non-fluorescent particle and the scattered light that is produced by the fluorescent particle. In this case, the scattered light peaks will be measured twice within a prescribed time interval. Additionally, the time t1 at which the measurement begins with the scattered light photodetecting element 50 detecting the scattered light is different from the time t2 at which the fluorescent light detecting element 20A and/or 20B begins measuring through detecting the fluorescent light.

Figure 26:
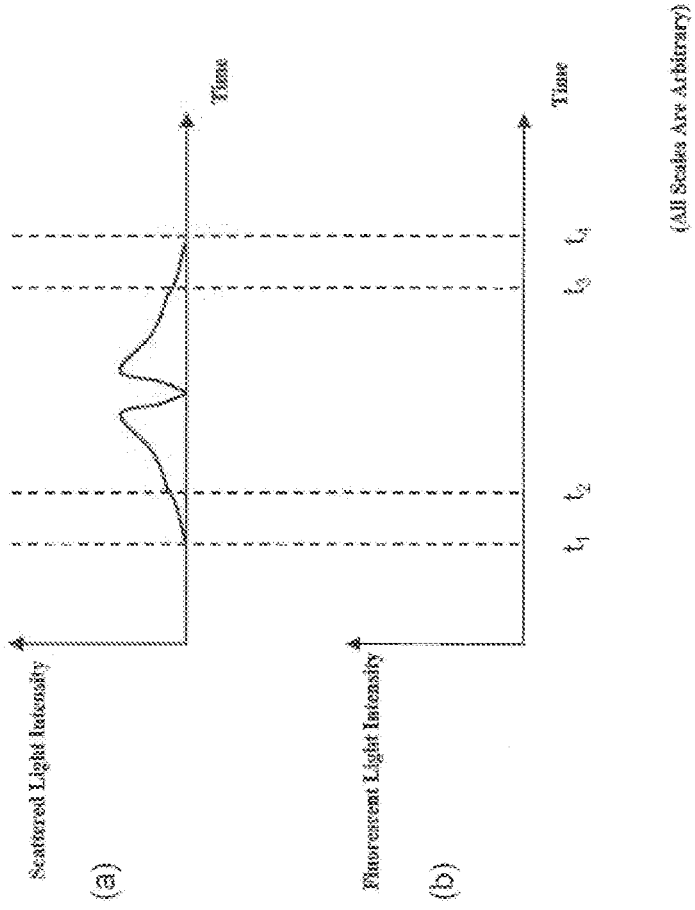
FIG. 26 is a graph illustrating schematically changes in time of the received light intensities for scattered light and fluorescent light when two non-fluorescent particles pass through the beam cross section of the excitation light, producing destructive interference, in relation to the Another Example according to the present disclosure.

FIGS. 26 (a) and (b) illustrate the temporal variation in the scattered light that is detected by the scattered light photodetecting element 50 and the temporal variation in the fluorescent light intensity detected by the fluorescent light detecting element 20A or 20B when two non-fluorescent particles pass through the cross-section of the excitation beam and destructive interference is produced between the scattered lights that are produced by the two non-fluorescent particles. In this case, the scattered light peaks will be measured twice within a prescribed time interval. Moreover, the intensity of the fluorescent light detected by the fluorescent light detecting element 20A or 20B remains at essentially zero.

Figure 27:
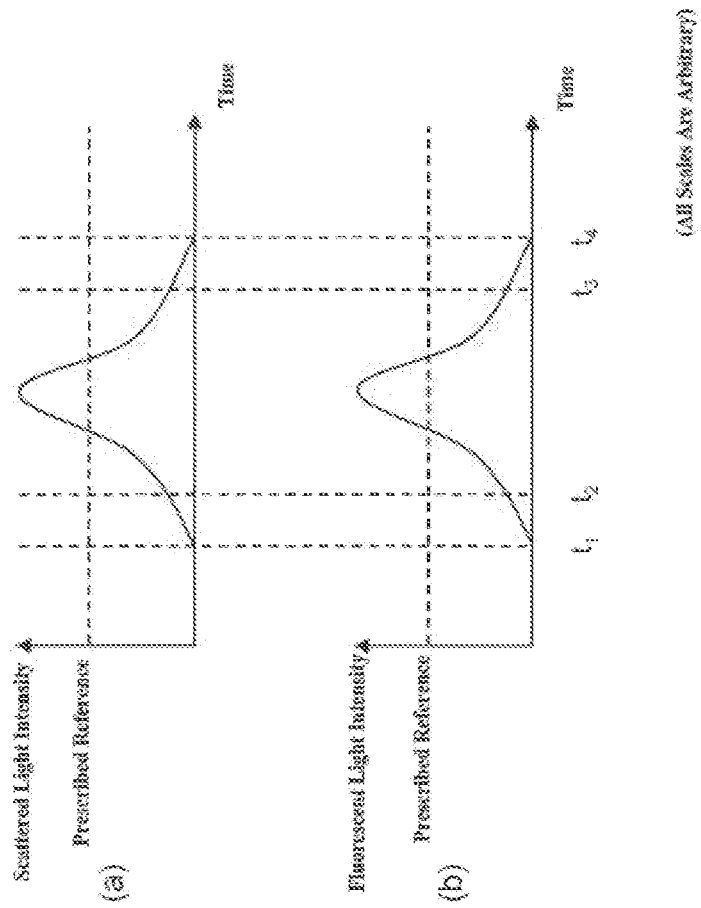
FIG. 27 is a graph illustrating schematically changes in time of the received light intensities for scattered light and fluorescent light when two fluorescent particles pass through the beam cross section of the excitation light, producing constructive interference, in relation to the Another Example according to the present disclosure.

FIGS. 27 (a) and (b) illustrate the temporal variation in the scattered light that is detected by the scattered light photodetecting element 50 and the temporal variation in the fluorescent light intensity detected by the fluorescent light detecting element 20A and/or 20B when two fluorescent particles pass through the cross-section of the excitation beam and constructive interference is produced between the scattered lights that are produced by the two fluorescent particles. In this case the temporal variation of the intensity of the scattered light, which is continuously measured without interruption across the prescribed time, will be equal to or greater than the prescribed standard for the scattered light. Additionally, the temporal variation of the intensity of the fluorescent light, which is continuously measured without interruption across the prescribed time, will be equal to or greater than the prescribed standard for the fluorescent light. Additionally, the time t1 at which the measurement begins with the scattered light photodetecting element 50 detecting the scattered light is essentially the same as the time t1 at which the fluorescent light detecting element 20A and/or 20B begins measuring through detecting the fluorescent light. Furthermore, the time t4 that is the end of the measurement, when the scattered light photodetecting element 50 ceases detecting scattered light, is essentially equal to the time t4 at which the fluorescent light detecting element 20A and/or 20B ends the measurement because fluorescent light ceases to be detected. Because of this, the times over which the scattered light in the fluorescent light are measured will be essentially equal.

Figure 28:
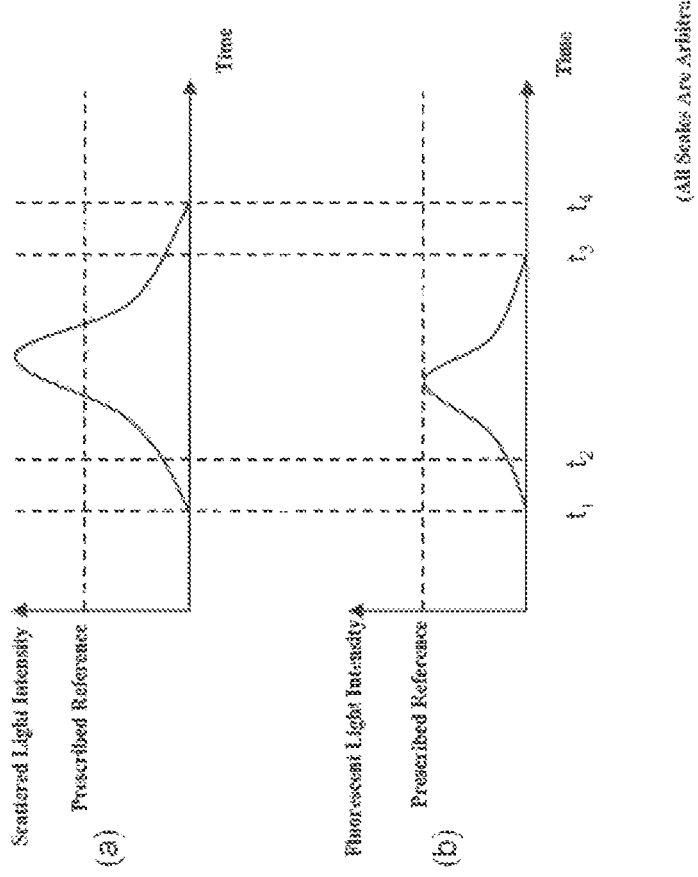
FIG. 28 is a graph illustrating schematically changes in time of the received light intensities for scattered light and fluorescent light when, following a single fluorescent particle, a single non-fluorescent particle passes through the beam cross section of the excitation light, producing constructive interference, in relation to the Another Example according to the present disclosure.

FIGS. 28 (a) and (b) illustrate the temporal variation in the scattered light that is detected by the scattered light photodetecting element 50 and the temporal variation in the fluorescent light intensity detected by the fluorescent light detecting element 20A and/or 20B when one non-fluorescent particle following one fluorescent particle pass through the cross-section of the excitation beam and constructive interference is produced between the scattered light that is produced by the fluorescent particle and the scattered light that is produced by the non-fluorescent particle. In this case the temporal variation of the intensity of the scattered light, which is continuously measured without interruption across the prescribed time, will be equal to or greater than the prescribed standard for the scattered light. Additionally, the time t4 at which the measurement ends when the scattered light photodetecting element 50 ceases to detect scattered light is different from the time t3 when the measurement by the fluorescent light detecting element 20A or 20B is completed because it ceases to detect fluorescent light, and the lengths of the times over which the scattered light and the fluorescent light were measured are different.

Figure 29:
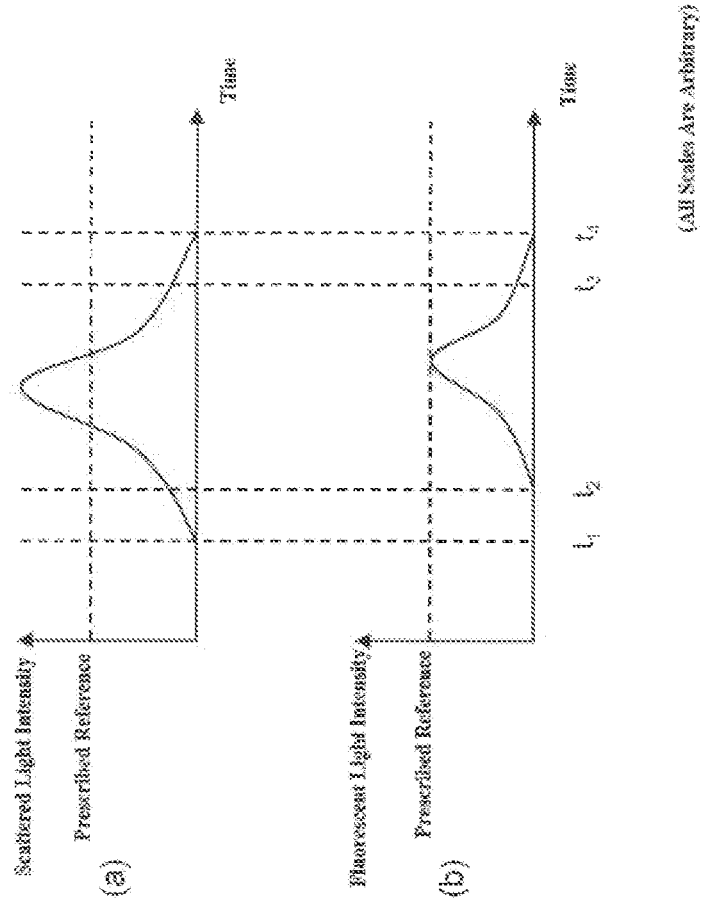
FIG. 29 is a graph illustrating schematically changes in time of the received light intensities for scattered light and fluorescent light when, following a non-single fluorescent particle, a single fluorescent particle passes through the beam cross section of the excitation light, producing constructive interference, in relation to the Another Example according to the present disclosure.

FIGS. 29 (a) and (b) illustrate the temporal variation in the scattered light that is detected by the scattered light photodetecting element 50 and the temporal variation in the fluorescent light intensity detected by the fluorescent light detecting element 20A and/or 20B when one fluorescent particle following one non-fluorescent particle pass through the cross-section of the excitation beam and constructive interference is produced between the scattered light that is produced by the non-fluorescent particle and the scattered light that is produced by the fluorescent particle. In this case the temporal variation of the intensity of the scattered light, which is continuously measured without interruption across the prescribed time, will be equal to or greater than the prescribed standard for the scattered light. Additionally, the time t1 at which the measurement begins with the scattered light photodetecting element 50 detecting the scattered light is different from the time t2 at which the fluorescent light detecting element 20A and/or 20B begins measuring through detecting the fluorescent light. Because of this, the times over which the scattered light in the fluorescent light are measured will be different.

Figure 30:
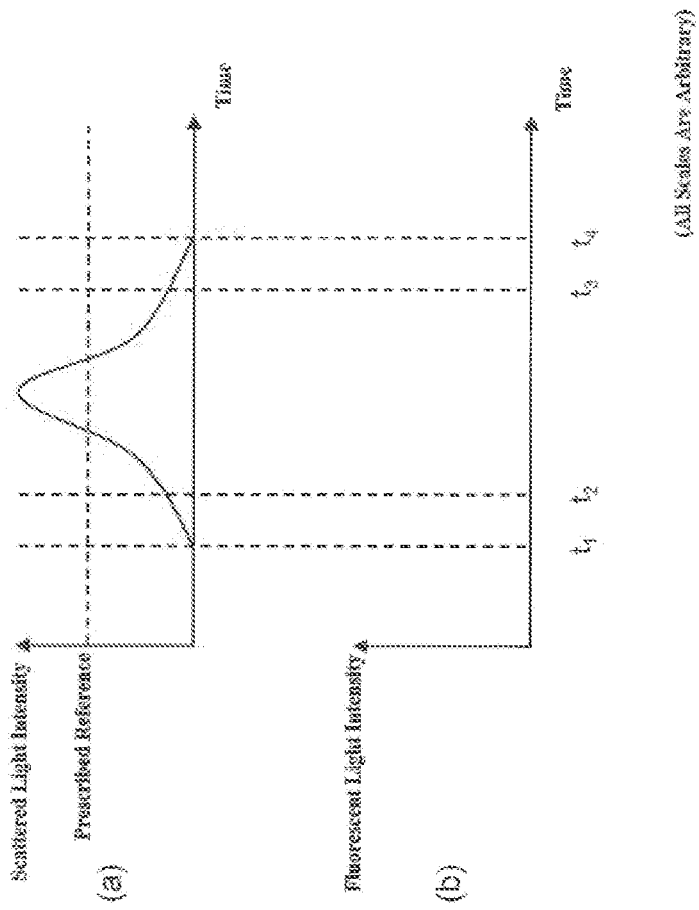
FIG. 30 is a graph illustrating schematically changes in time of the received light intensities for scattered light and fluorescent light when two non-fluorescent particles pass through the beam cross section of the excitation light, producing constructive interference, in relation to the Another Example according to the present disclosure.

FIGS. 30 (a) and (b) illustrate the temporal variation in the scattered light that is detected by the scattered light photodetecting element 50 and the temporal variation in the fluorescent light intensity detected by the fluorescent light detecting element 20A or 20B when two non-fluorescent particles pass through the cross-section of the excitation beam and constructive interference is produced between the scattered lights that are produced by the two non-fluorescent particles. In this case the temporal variation of the intensity of the scattered light, which is continuously measured without interruption across the prescribed time, will be equal to or greater than the prescribed standard for the scattered light. Moreover, the intensity of the fluorescent light detected by the fluorescent light detecting element 20A or 20B remains at essentially zero.

The other structural elements in the particle detecting device 1 according to the Another Example are identical to those in the Example. The particle detecting device 1 can count a plurality of particles, separated into fluorescent particles and non-fluorescent particles, even if the excitation beam is a Gaussian beam.

Other Examples

Figure 31:
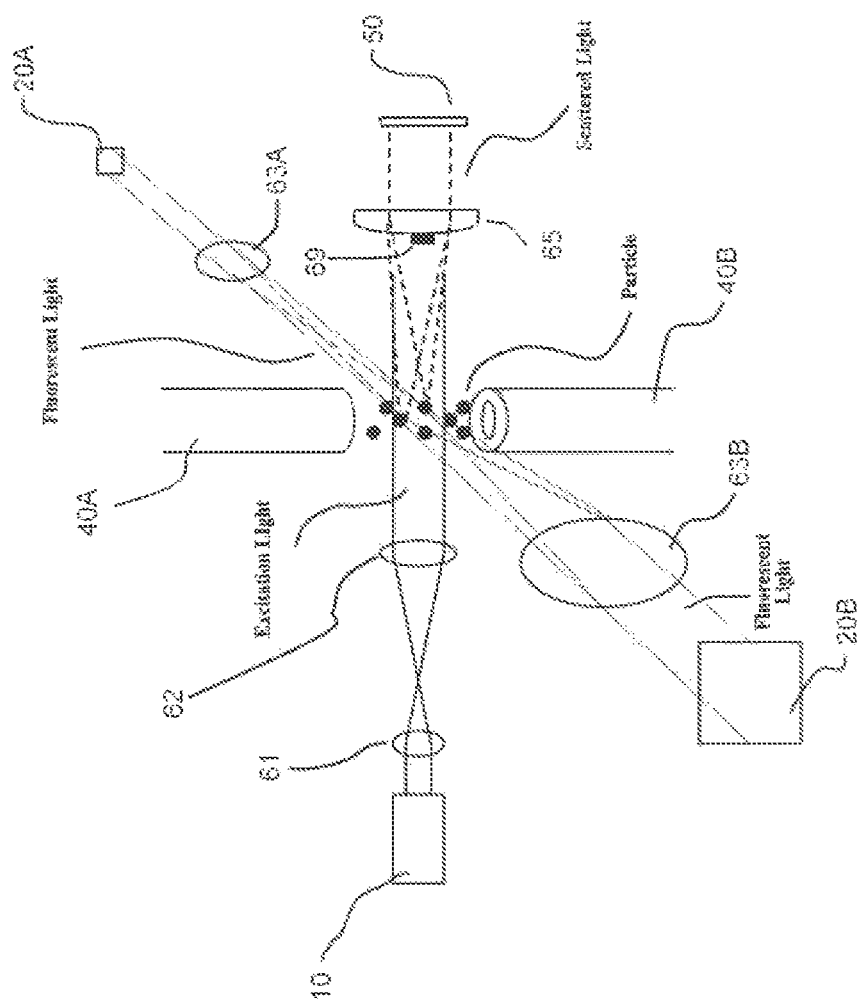
FIG. 31 is a schematic diagram of an optics system of a particle detecting device according to an alternate example according to the present disclosure.
Figure 32:
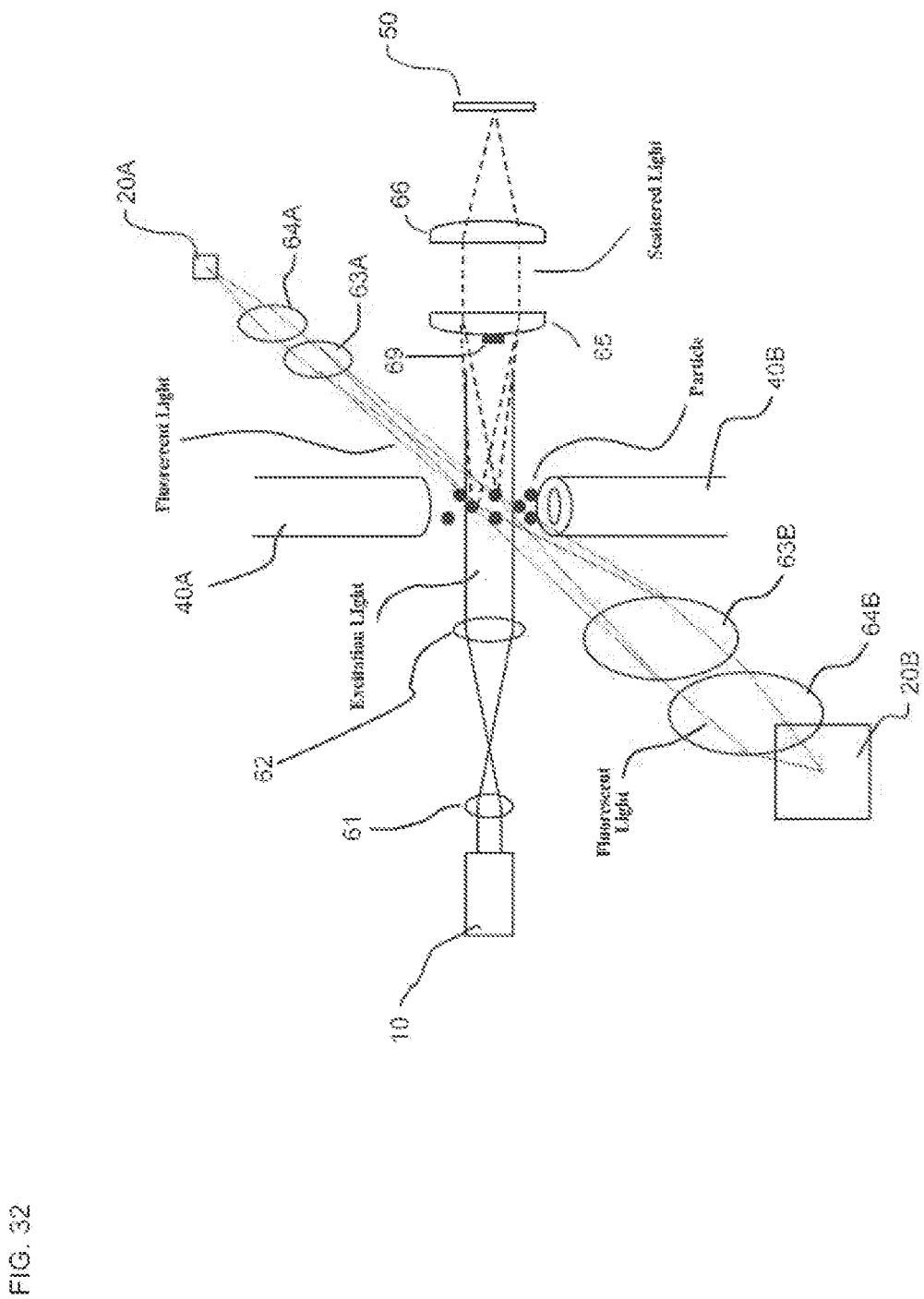
FIG. 32 is a schematic diagram of an optics system of a particle detecting device according to another alternate example according to the present disclosure.
Figure 33:
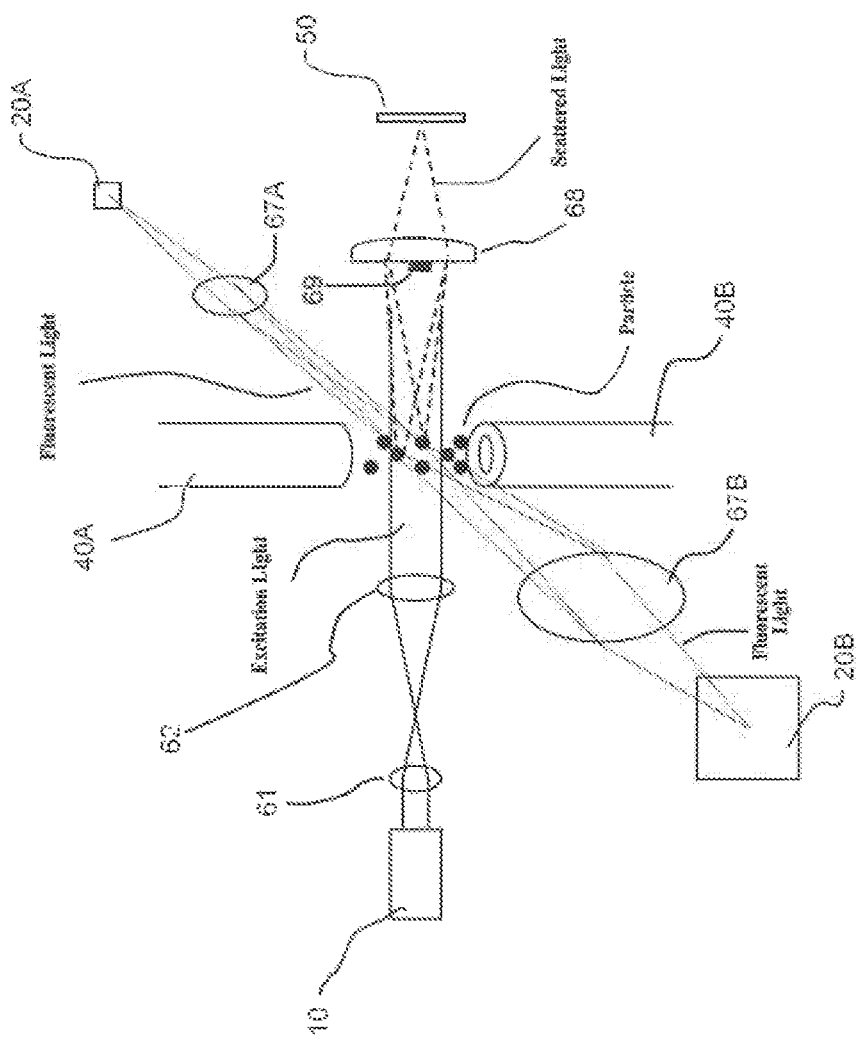
FIG. 33 is a schematic diagram of an optics system of a particle detecting device according to yet another alternate example according to the present disclosure.

While there are descriptions of examples as set forth above, the descriptions and drawings that form a portion of the disclosure are not to be understood to limit the present disclosure. A variety of alternate examples and exemplary operating technologies should be obvious to those skilled in the art. For example, the location wherein the particle detecting device 1 according to the present example is not limited to being a clean room. Moreover, the optics system of the particle detecting device 1 is not limited to that which is illustrated in FIG. 3. For example, as illustrated in FIG. 31, a collimating lens 63A may be disposed in front of the fluorescent light detecting element 20A, a collimating lens 63B may be disposed in front of the fluorescent light detecting element 20B, and a collimating lens 65 may be disposed in front of the scattered light photodetecting element 50. Conversely, as illustrated in FIG. 32, a collimating lens 63A and a focusing lens 64A may be disposed in front of the fluorescent light detecting element 20A, a collimating lens 63B and a focusing lens 64B may be disposed in front of the fluorescent light detecting element 20B, and a collimating lens 65 and a focusing lens 66 may be disposed in front of the scattered light photodetecting element 50. On the other hand, as illustrated in FIG. 33, a focusing lens 67A may be disposed in front of the fluorescent light detecting element 20A, a focusing lens 67B may be disposed in front of the fluorescent light detecting element 20B, and a focusing lens 68 may be disposed in front of the scattered light photodetecting element 50. In this way, the present disclosure should be understood to include a variety of examples, and the like, not set forth herein.

The invention claimed is:

1. A particle detecting device comprising:
  a light source that illuminates, with an excitation beam, a fluid that contains a plurality of particles;
  a fluorescence measuring instrument that measures, at at least two different wavelengths, fluorescence that is produced in a region that is illuminated by the excitation beam;
  a scattered light measuring instrument that measures scattered light that is produced in a region that is illuminated by the excitation beam;
  an interference status evaluating portion that evaluates whether the scattered light that is measured is producing constructive interference or producing destructive interference; and
  a particle counting portion that counts a plurality of particles depending on the measured interference of the measured light, and counts fluorescent particles that are subject to detection, from among the plurality of particles, based on a wavelength of fluorescent measured,
  wherein if the measured scattered light is producing constructive interference and no florescent light is measured, the particle counting portion evaluates that all of the plurality of particles is non-fluorescent particles.

2. The particle detecting device as set forth in claim 1, wherein:
  if peaks for scattered light are measured multiple times due to destructive interference, and the time of the beginning of measurement of the fluorescent light and the time of the beginning of measurement of the first scattered light are different or the time of the end of measurement of the fluorescent light and the time of the end of measurement of the last scattered light are different, the particle counting portion evaluates that some portion of the plurality of particles is fluorescent particles.

3. The particle detecting device as set forth in claim 1, wherein:
  if peaks of the scattered light are measured multiple times due to destructive interference and no florescent light is measured, the particle counting portion evaluates that all of the plurality of particles is non-fluorescent particles.

4. The particle detecting device as set forth in claim 1, wherein:
  if scattered light is measured over a prescribed time and temporal variation of the intensity of the scattered light is below that which is prescribed, the interference status evaluating portion evaluates that the measured scattered light is not producing interference.

5. A particle detecting device comprising:
  a light source that illuminates, with an excitation beam, a fluid that contains a plurality of particles;

a fluorescence measuring instrument that measures, at at least two different wavelengths, fluorescence that is produced in a region that is illuminated by the excitation beam;

a scattered light measuring instrument that measures scattered light that is produced in a region that is illuminated by the excitation beam;

an interference status evaluating portion that evaluates whether the scattered light that is measured is producing constructive interference or producing destructive interference; and a particle counting portion that counts a plurality of particles depending on the measured interference of the measured light, and counts fluorescent particles that are subject to detection, from among the plurality of particles, based on a wavelength of fluorescent measured, wherein if peaks for scattered light are measured multiple times due to destructive interference, the time of the beginning of measurement of the fluorescent light and the time of the beginning of measurement of the first scattered light are essentially equal, and the time of the end of measurement of fluorescent light and the time of the end of measurement of the last scattered light are essentially equal, the particle counting portion evaluates that essentially all of the plurality of particles is fluorescent particles.

6. A particle detecting method, comprising the steps of:

illuminating, by a light source with an excitation beam, a fluid that contains a plurality of particles;

measuring, by a fluorescence at at least two different wavelengths, fluorescence that is produced in a region that is illuminated by the excitation beam;

measuring, by a scattered light measuring instrument, scattered light that is produced in a region that is illuminated by the excitation beam;

evaluating, by an interference status evaluating portion, whether the scattered light that is measured is producing constructive interference or producing destructive interference; and counting, by a particle counting portion, a plurality of particles depending on the measured interference of the measured light, and counting fluorescent particles that are subject to detection, from among the plurality of particles, based on a wavelength of fluorescent measured, wherein if the measured scattered light is producing constructive interference and no florescent light is measured, there is an evaluation that all of the plurality of particles is non-fluorescent particles.

7. The particle detecting method as set forth in claim 6, wherein:

if peaks for scattered light are measured multiple times due to destructive interference, the time of the beginning of measurement of the fluorescent light and the time of the beginning of measurement of the first scattered light are essentially equal, and the time of the end of measurement of fluorescent light and the time of the end of measurement of the last scattered light are essentially equal, there is an evaluation that essentially all of the plurality of particles is fluorescent particles.

8. The particle detecting method as set forth in claim 6, wherein:

if peaks for scattered light are measured multiple times due to destructive interference, and the time of the beginning of measurement of the fluorescent light and the time of the beginning of measurement of the first scattered light are different or the time of the end of measurement of the fluorescent light and the time of the end of measurement of the last scattered light are different, there is an evaluation that some portion of the plurality of particles is fluorescent particles.

9. The particle detecting method as set forth in claim 6, wherein:

if peaks of the scattered light are measured multiple times due to destructive interference and no florescent light is measured, there is an evaluation that all of the plurality of particles is non-fluorescent particles.

10. The particle detecting method as set forth in claim 6, wherein:

if scattered light is measured over a prescribed time and temporal variation of the intensity of the scattered light is below that which is prescribed, there is an evaluation that the measured scattered light is not producing interference.

* * * * *